(12) United States Patent
Krietzman

(10) Patent No.: US 10,118,013 B2
(45) Date of Patent: Nov. 6, 2018

(54) RECHARGEABLE PORTABLE AROMATHERAPY VAPORIZERS

(71) Applicant: Mark Krietzman, Palos Verdes Estates, CA (US)

(72) Inventor: Mark Krietzman, Palos Verdes Estates, CA (US)

( * ) Notice: Subject to any disclaimer, the term of this patent is extended or adjusted under 35 U.S.C. 154(b) by 0 days.

(21) Appl. No.: 15/785,308

(22) Filed: Oct. 16, 2017

(65) Prior Publication Data
US 2018/0085551 A1 Mar. 29, 2018

Related U.S. Application Data

(63) Continuation-in-part of application No. 15/045,478, filed on Feb. 17, 2016, now Pat. No. 9,826,780.

(60) Provisional application No. 62/485,995, filed on Apr. 16, 2017, provisional application No. 62/435,753, filed on Dec. 17, 2016, provisional application No. 62/270,557, filed on Dec. 21, 2015, provisional application No. 62/208,786, filed on Aug. 23, 2015, provisional application No. 62/184,396, filed on Jun. 25, 2015, provisional application No. 62/127,817, filed on Mar. 3, 2015, provisional application No. 62/116,926, filed on Feb. 17, 2015.

(51) Int. Cl.
| | |
|---|---|
| *A61M 21/02* | (2006.01) |
| *A61M 11/04* | (2006.01) |
| *H05B 1/02* | (2006.01) |
| *A61M 21/00* | (2006.01) |

(52) U.S. Cl.
CPC .......... *A61M 21/02* (2013.01); *A61M 11/042* (2014.02); *H05B 1/0252* (2013.01); *A61M 2021/0016* (2013.01); *A61M 2205/3334* (2013.01); *A61M 2205/3368* (2013.01); *A61M 2205/3584* (2013.01); *A61M 2205/3592* (2013.01); *A61M 2205/584* (2013.01); *A61M 2205/587* (2013.01); *A61M 2205/7545* (2013.01); *A61M 2205/8206* (2013.01)

(58) Field of Classification Search
CPC ..................................................... A24F 47/008
See application file for complete search history.

(56) References Cited

U.S. PATENT DOCUMENTS

| | | | | |
|---|---|---|---|---|
| 9,414,629 | B2 * | 8/2016 | Egoyants | A24F 47/008 |
| 9,516,899 | B2 * | 12/2016 | Plojoux | A24F 47/008 |
| 9,609,894 | B2 * | 4/2017 | Abramov | A24F 47/008 |
| 9,675,117 | B2 * | 6/2017 | Li | A61M 15/06 |
| 2014/0202476 | A1 * | 7/2014 | Egoyants | A24F 47/008 |
| | | | | 131/329 |
| 2014/0366898 | A1 * | 12/2014 | Monsees | A24F 47/008 |
| | | | | 131/329 |
| 2016/0198771 | A1 * | 7/2016 | Goggin | A24F 47/008 |
| | | | | 131/329 |

(Continued)

*Primary Examiner* — Ross Gushi

(57) ABSTRACT

Disclosed herein are aspects of portable vaporizers and isolated vapor dispensers wherein material in the vapor dispenser is placed in the fluid pathway of heated air from a convection heat source such as a furnace. A printed circuit board in signal communications with temperature sensor controls the temperature produced by heating elements in the furnace. A rechargeable battery power supply is mounted in a body to supply power the heating element. The vapor dispenser is removable and may be disposable. A smell reducing accessory module reversibly mates with the body of the vaporizer.

17 Claims, 13 Drawing Sheets

(56) References Cited

U.S. PATENT DOCUMENTS

| | | | | |
|---|---|---|---|---|
| 2016/0255879 A1* | 9/2016 | Paprocki | .............. | H05B 1/0291 |
| 2016/0331033 A1* | 11/2016 | Hopps | .................. | A24F 47/008 |
| 2017/0108210 A1* | 4/2017 | Meinhart | .................. | F22B 1/30 |
| 2017/0119051 A1* | 5/2017 | Blandino | .............. | A24F 47/008 |
| 2017/0156407 A1* | 6/2017 | Abramov | .............. | A24F 47/008 |

* cited by examiner

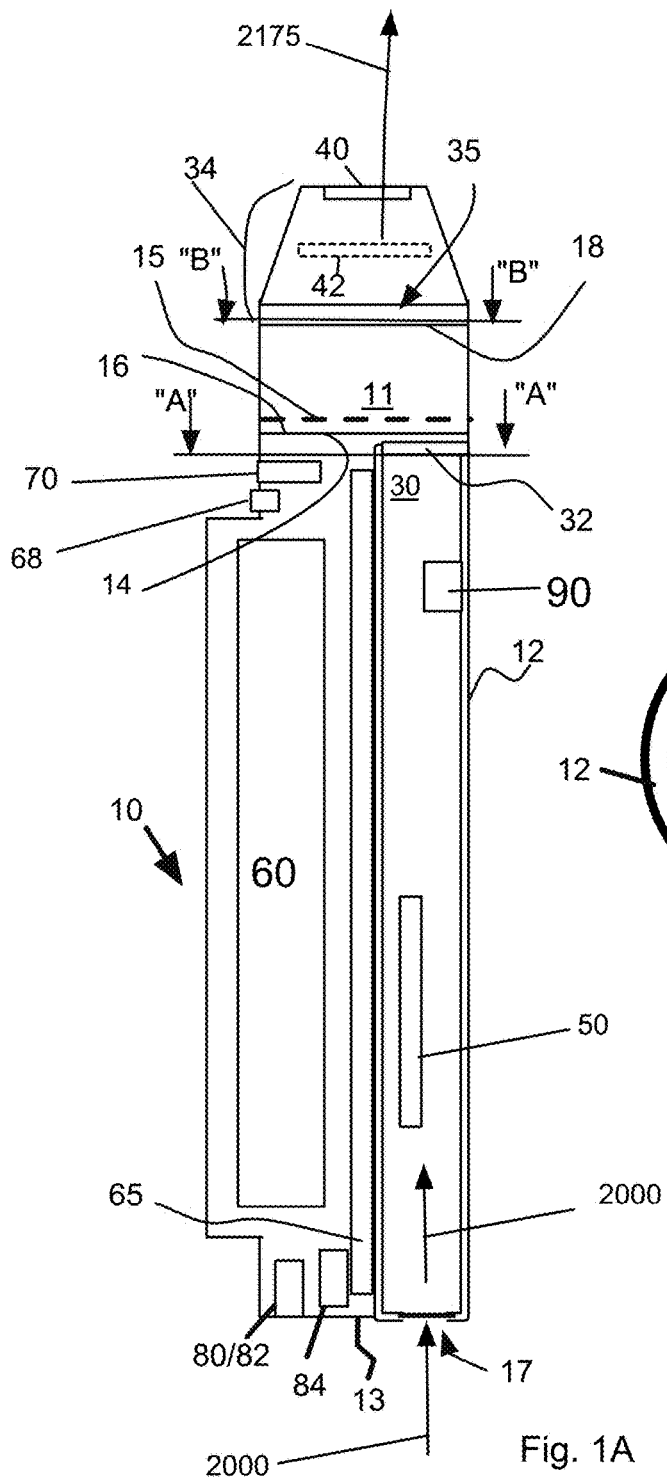
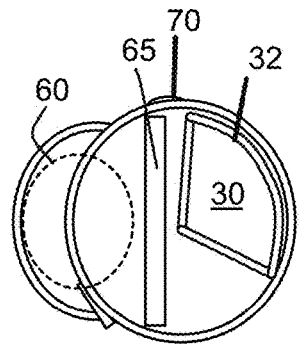
Fig. 1B
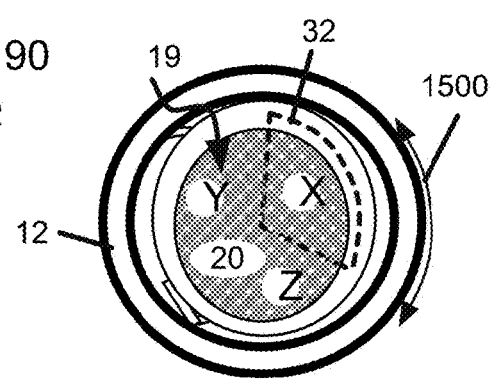
Fig. 1C
Fig. 1A

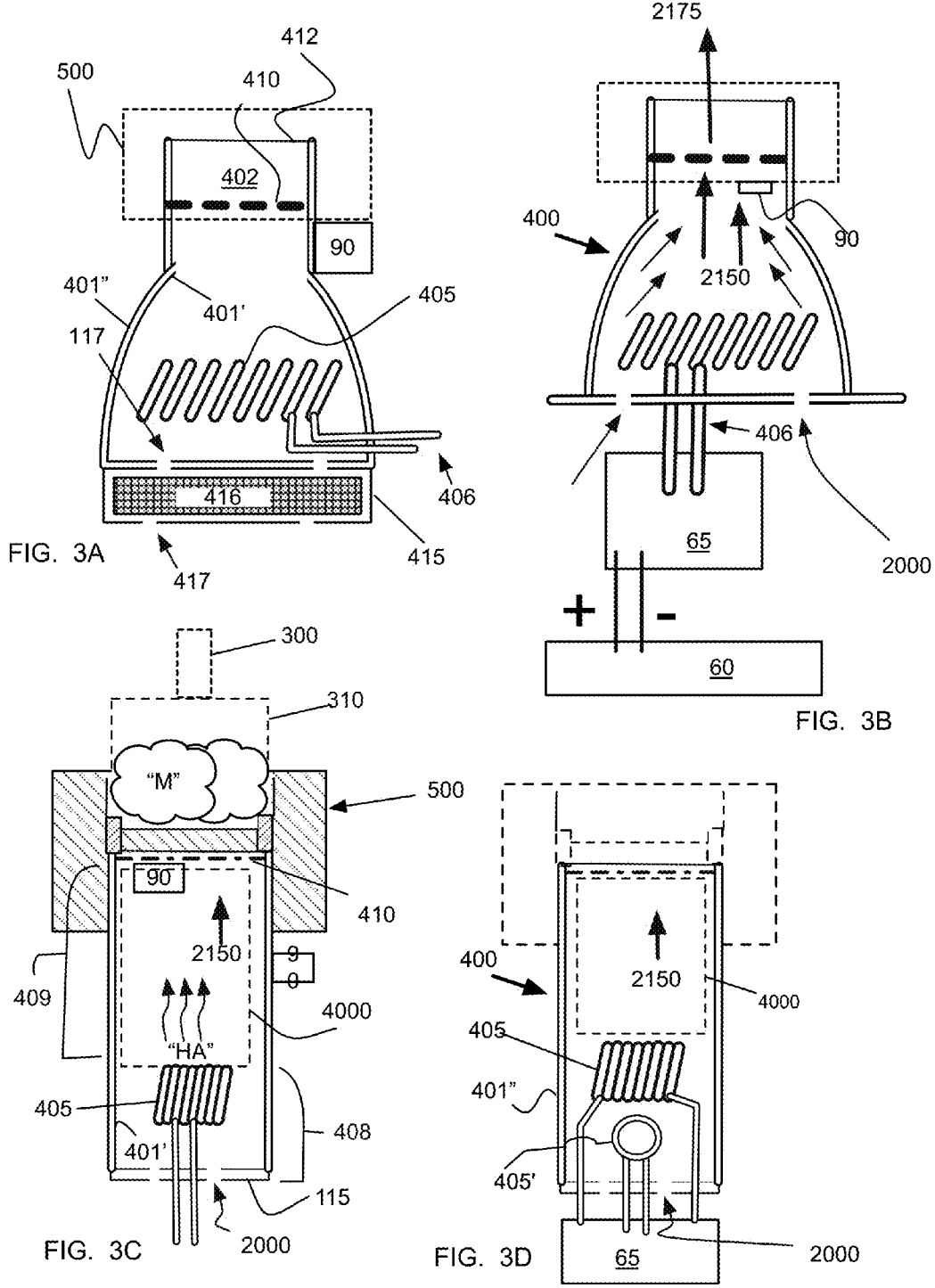

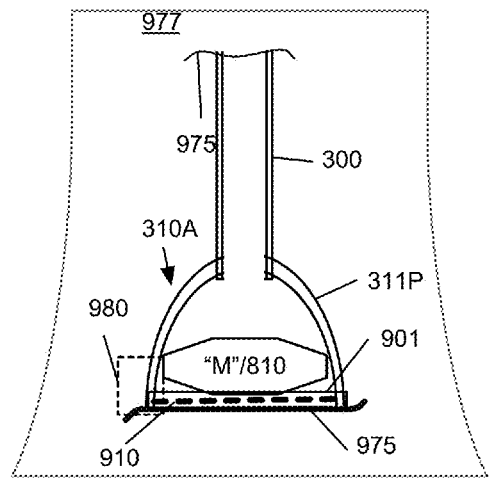
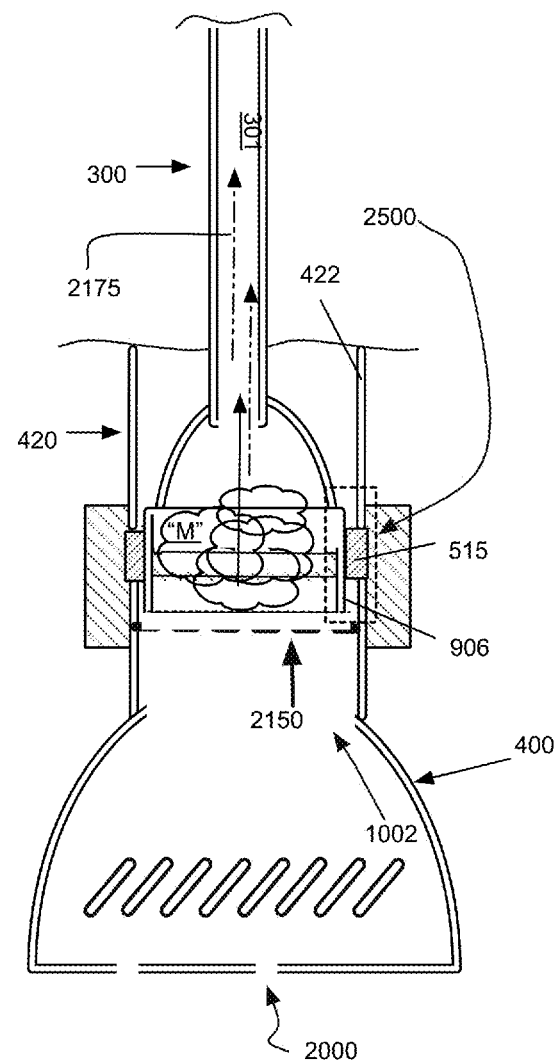
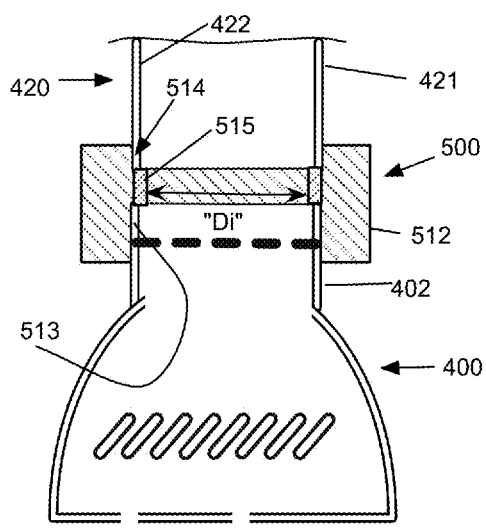
FIG. 4D
FIG. 5A
FIG. 5B

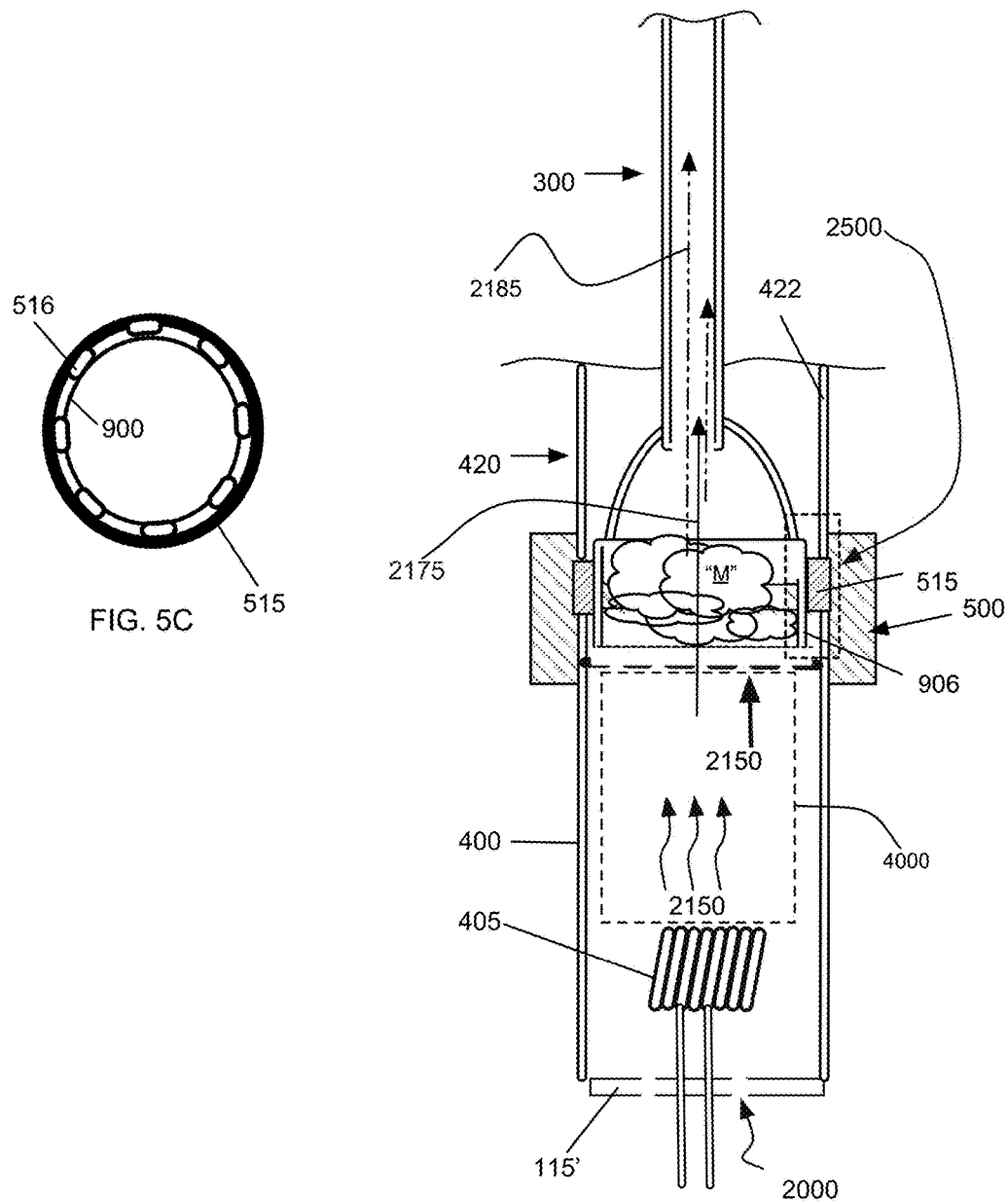

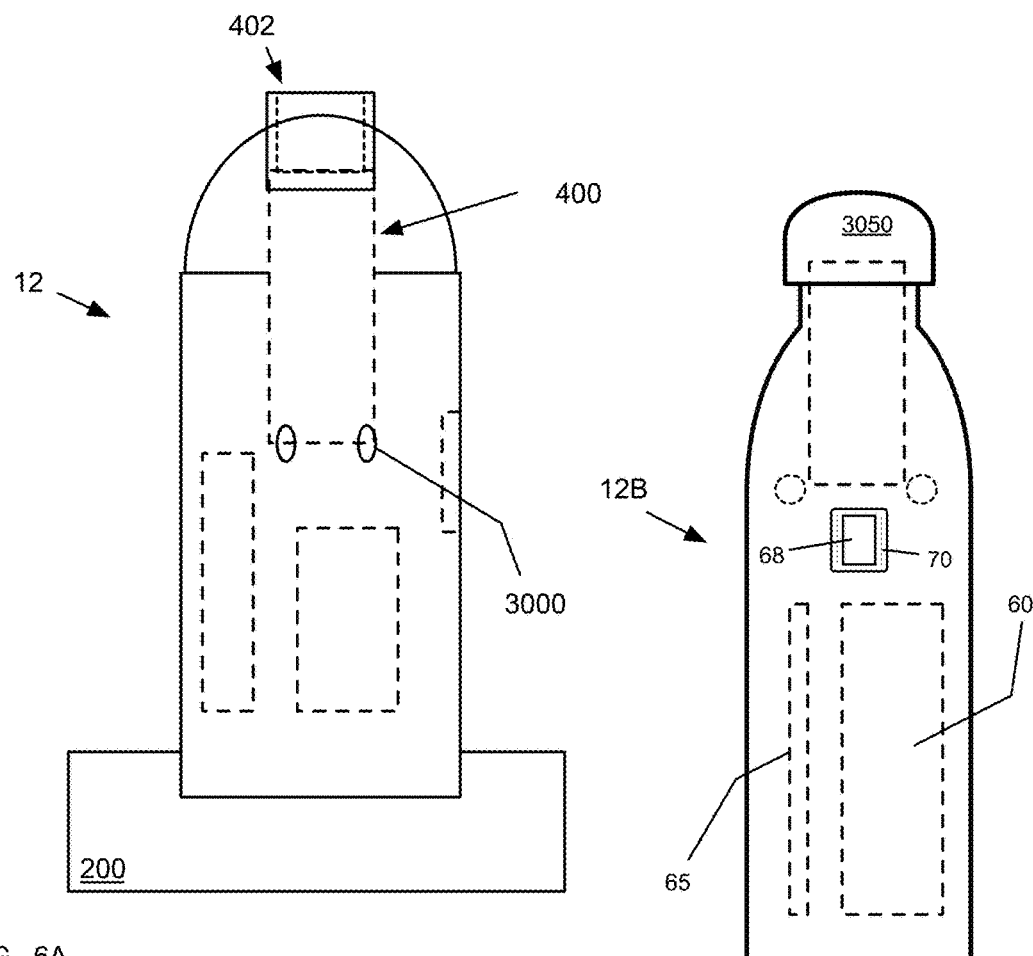
FIG. 6A
FIG. 6B
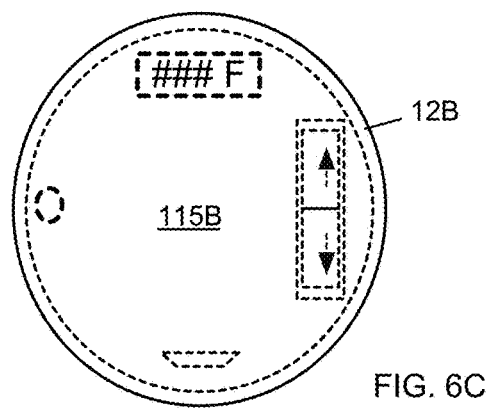
FIG. 6C

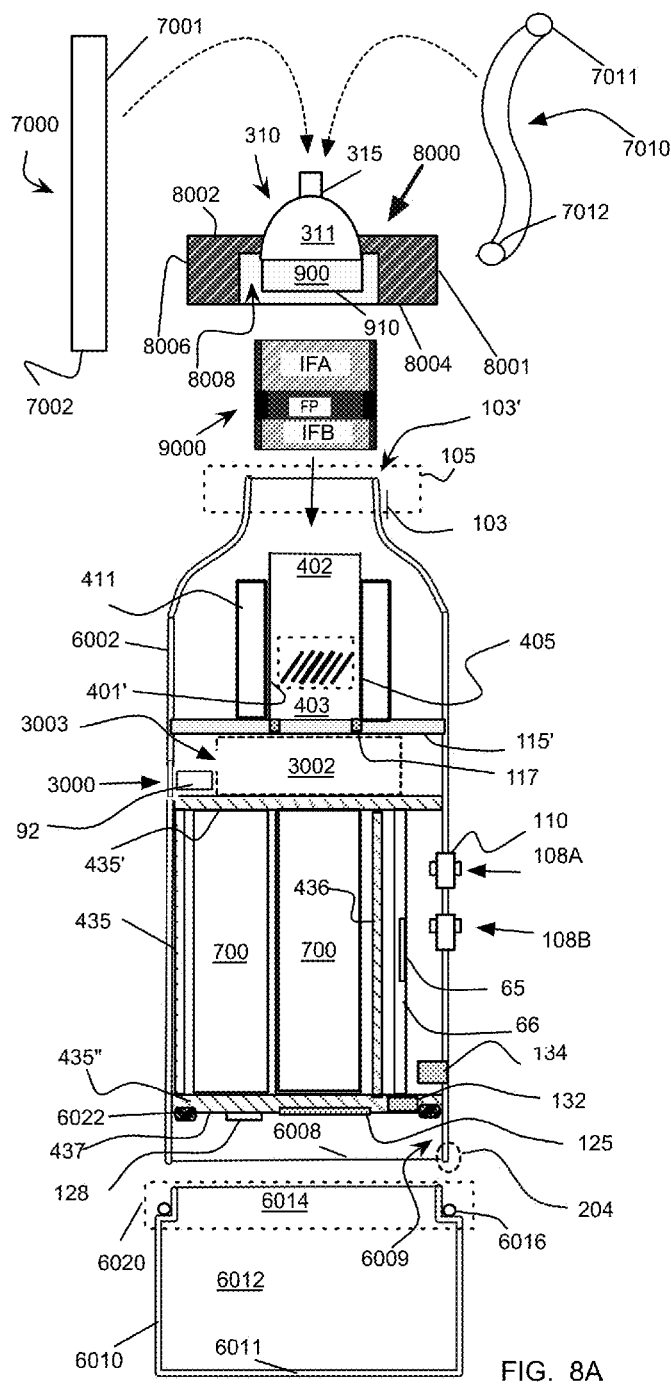
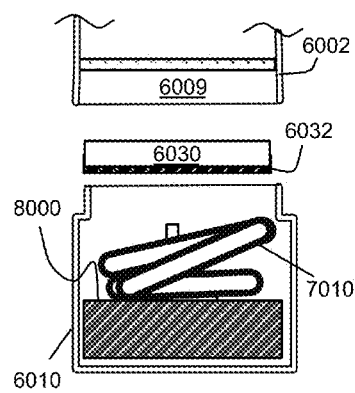
FIG. 8B
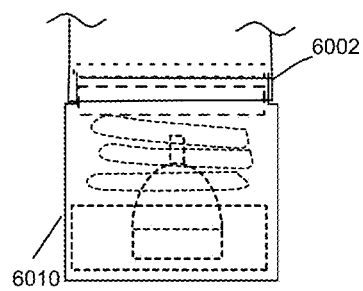
FIG. 8C
FIG. 8A

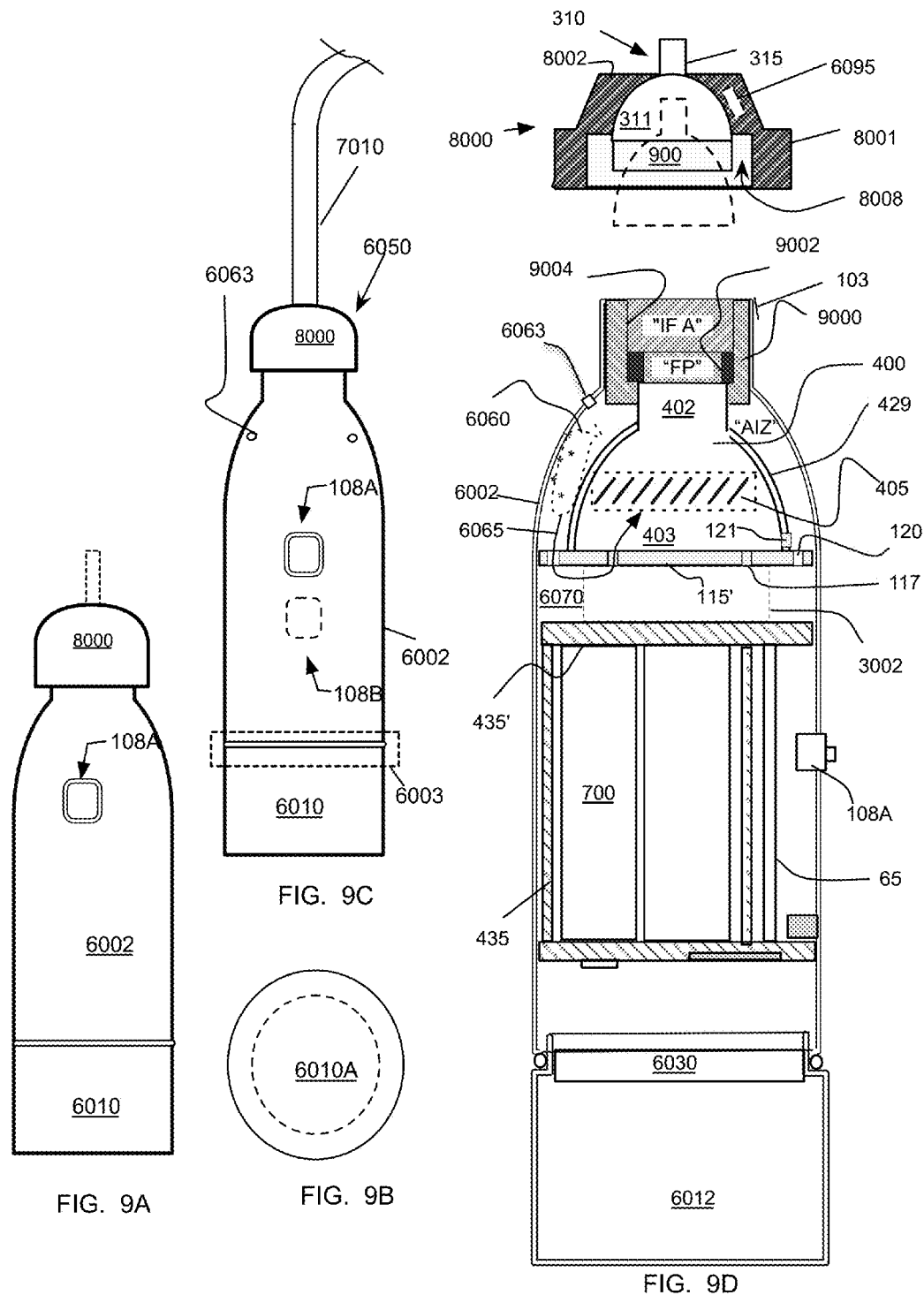

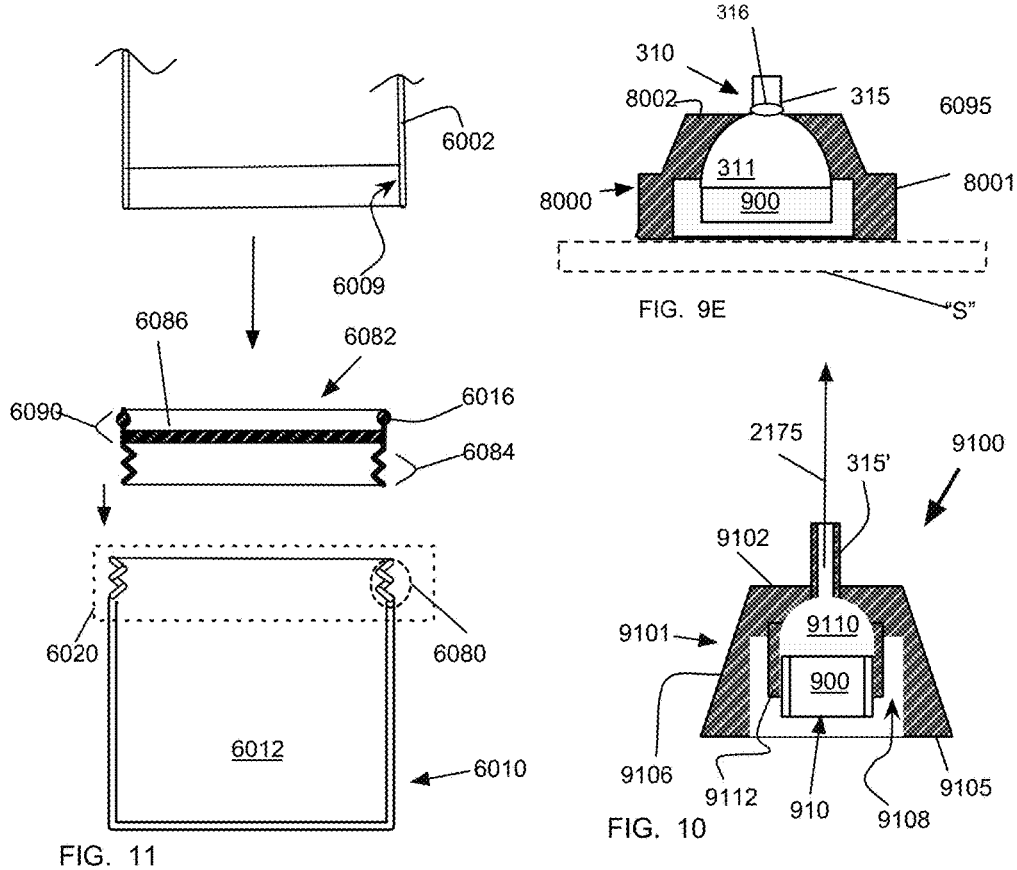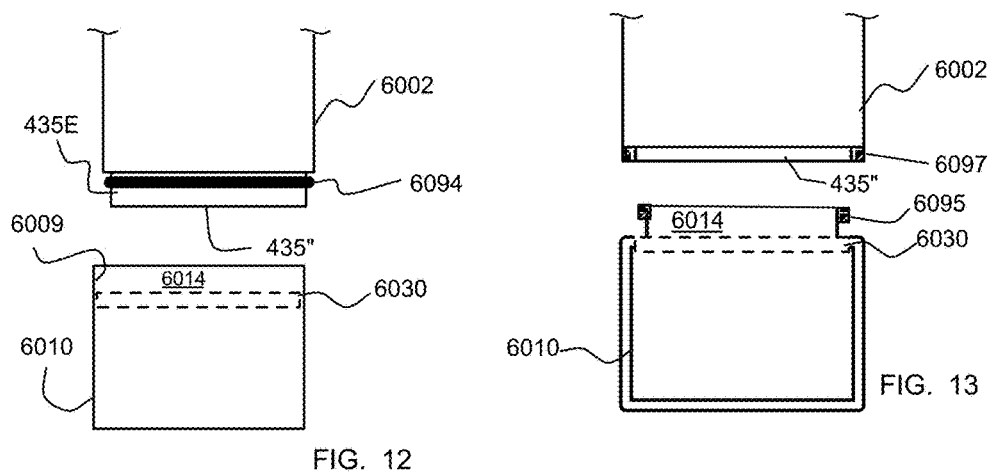

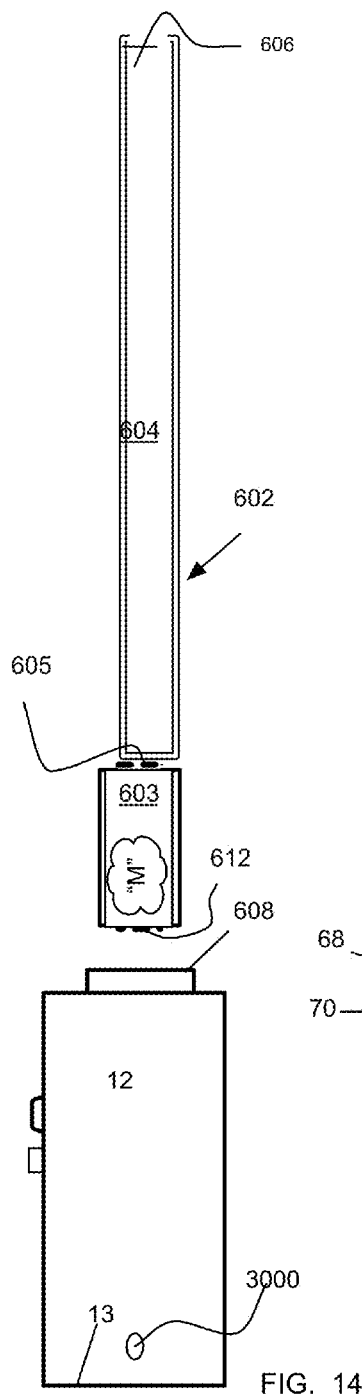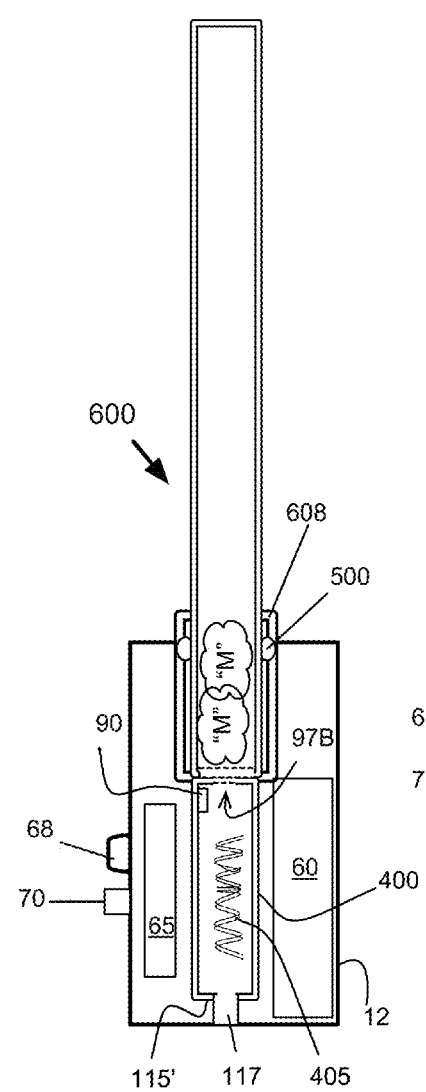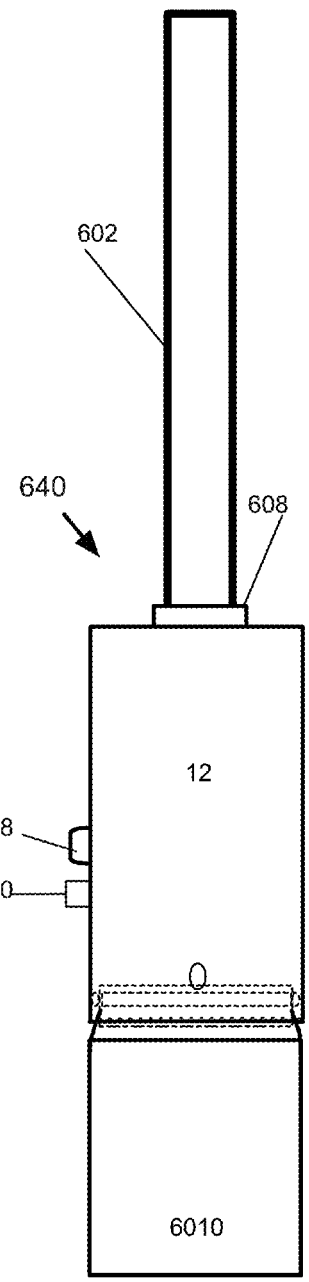
FIG. 14A
FIG. 14B
FIG. 15

RECHARGEABLE PORTABLE AROMATHERAPY VAPORIZERS

RELATED CASE

This application is a Continuation-in-part to United States ("U.S.") patent application Ser. No. 15/045,478 filed February 17, the disclosure of which is incorporated by reference as of fully set forth herein. This application also claims the priority to U.S. Provisional Patent Application Ser. No. 62/435,753 entitled RECHARGEABLE CONVECTION VAPORIZER Dec. 17, 2016, the disclosure of which is incorporated by reference herein in its entirety. This Application also claims priority to U.S. Provisional Patent Application Ser. No. 62/485,995 entitled RECHARGEABLE CONCENTRATING CONVECTION VAPORIZER filed Apr. 16, 2017 the disclosure of which is also hereby incorporated by reference their entirety as if fully set forth herein.

BACKGROUND OF THE DISCLOSURE

Field of the Disclosure

The present disclosure relates generally to a convection vaporizer for aromatherapy which dynamically heats air in a furnace and supplies it to a chamber containing organic material thereby releasing residues from essential oils, extracts and plant from the organic material without combustion.

Related Art

Vaporizer for plant based materials and essential oils and exist. Vaporizers allow aroma therapy or inhalation. Vaporizers which allow inhalation from a fluid pathway whereby gas containing the vapor without combustion by products through a fluid pathway from source of vapor to exists. Herbs and botanicals have been known in the art to be vaporized or burned to release organic material in the form of inhalable material.

Lavender vaporizes at 260° F. Tobacco vaporizes between 257° F. to 302° F.; Green tea vaporizes between about 175° C. to 185° C.; Valerian vaporizes at about 235° C.; Chamomile used to aid in the relief of anxiety vaporizes at about 380° F.; Peppermint vaporizes at about 255° F. Peppermint is also known to ease symptoms of allergies and asthma, in addition to alleviating some of the side effects that come along with the common cold or a sinus infection. Cannabis, has a range at which it can be heated to release different cannabinoids as vapor without burning the organic material. From below 200 F. to about 430 F.

In the following description of examples of implementations, reference is made to the accompanying drawings that form a part hereof, and which show, by way of illustration, specific implementations of the present disclosure that may be utilized. Other implementations may be utilized and structural changes may be made without departing from the scope of the present disclosure.

DISCLOSURE

A rechargeable, portable convection vaporizer is disclosed and aspects related to its temperature concentration, buffering and smell management.

It is appreciated by those skilled in the art that some of the circuits, components, controllers, modules, and/or devices of the system disclosed in the present application are described as being in signal communication with each other, where signal communication refers to any type of communication and/or connection between the circuits, components, modules, and/or devices that allows a circuit, component, module, and/or device to pass and/or receive signals and/or information from another circuit, component, module, and/or device. The communication and/or connection may be along any signal path between the circuits, components, modules, and/or devices that allows signals and/or information to pass from one circuit, component, module, and/or device to another and includes wireless or wired signal paths. The signal paths may be physical such as, for example, conductive wires, electromagnetic wave guides, attached and/or electromagnetic or mechanically coupled terminals, semi-conductive or dielectric materials or devices, or other similar physical connections or couplings. Additionally, signal paths may be non-physical such as free-space (in the case of electromagnetic propagation) or information paths through digital components where communication information is passed from one circuit, component, module, and/or device to another in varying analog and/or digital formats without passing through a direct electromagnetic connection. These information paths may also include analog-to-digital conversions ("ADC"), digital-to-analog ("DAC") conversions, data transformations such as, for example, fast Fourier transforms ("FFTs"), time-to-frequency conversations, frequency-to-time conversions, database mapping, signal processing steps, coding, modulations, demodulations, etc. The controller devices and smart devices disclosed herein operate with memory and processors whereby code is executed during processes to transform data, the computing devices run on a processor (such as, for example, controller or other processor that is not shown) which may include a central processing unit ("CPU"), digital signal processor ("DSP"), application specific integrated circuit ("ASIC"), field programmable gate array ("FPGA"), microprocessor, etc. Alternatively, portions DCA devices may also be or include hardware devices such as logic circuitry, a CPU, a DSP, ASIC, FPGA, etc. and may include hardware and software capable of receiving and sending information.

Some aspects of exemplary implementations of vaporizers with isolated fluid pathway are disclosed including placing within a generally hollow body having a top opening and an interface fluidly connecting the top opening with a duct inside the body; a concentrating furnace with a heating element therein having a open top and a partially sealed bottom with one or more air intakes and the duct has an internal diameter. An insulator member is interposed between the distal end of the duct and the top of the furnace; a duct insertable chamber connected to a fluid pathway; and, a control circuit board in signal communication with electrical components in the body including battery on/off switch, illumination communication means, heating element and sensors. In some instances the illumination communications means is one or more light emitting diodes. In some instance the furnace is shaped to concentrate the heated air during operation of the furnace heating element.

Some aspects of exemplary implementations of portable aromatherapy vaporizers include a generally hollow body with an open. A portable power supply inside the body and a heating system within the body having furnace, a heating element inside the furnace, a temperature sensor, a controller in signal communication with at least the sensor, heating element, power supply and on/off control. The furnace having a vented floor partially sealing off the bottom of the furnace. A connection interface gasket (CIG) providing a fluid pathway from the open top to furnace. a vapor dispenser including an insulator body, a material chamber with an exit port the vapor dispenser configured to removably mate with the CIG through the open top whereby the on/off switch is in signal communication with the control board and the control board controls the heating of the heating element based on input from the temperature sensor via the heating element and wherein during operation heated air within the heating system moves from the heating element to an air buffer region and collects until a pressure differential causes the heated air to move into the material chamber through material thereby producing vapor and heated air.

Some aspects of exemplary implementations of portable aromatherapy vaporizers include a generally hollow body with an open top a recess above a bottom edge including a portable power supply and a heating system within the body. The heating system a heating element inside a furnace, a temperature sensor, a controller in signal communication with at least the sensor, heating element, power supply and an on/off control. The furnace is partially sealed at its bottom and vents are provided therein to allow airflow. A connection interface gasket (CIG) providing a fluid pathway from the furnace to the open top of the body. A vapor dispenser including an insulator body, a material chamber with an exit port which is configured to removably mate with the CIG through the open top. The on/off switch is in signal communication with the control board and the control board controls the heating of the heating element based on input from at least the temperature sensor. During operation heated air within the heating system moves from the heating element to an air buffer region and collects until a pressure differential causes the heated air to move into the material chamber through material thereby producing vapor and heated air. The vapor dispenser is one of refillable and disposable. In some instances a generally hollow accessory module of a size and shape to contain at least the vapor dispenser and inhalation tube is mated with the body at the recess. The module having an open top region and closed bottom (which reversibly mates with the recess. In some instances the open top of the module may be separately sealed with a lid. In other instances the bottom of the vaporizer body seals the module.

To the above exemplars at least one illumination means in signal communication with the control board which produces an illumination visible on the exterior of the body may be added. In some instances a fan to direct air into the vented floor to the interior of the furnace is included. When a fan is added either a dual function single switch ((which controls heating and fan) or a second on/off control for the fan may be added.

Some aspects of exemplary implementations of portable aromatherapy vaporizers vapor dispensers include a material chamber which may be disassociated form an insulator body. The disassociation supports cleaning and refilling of the material chamber. The material chamber includes a bottom cup attached to a shaped container. The material chamber is removably fixed within the insulator body placing the cup above the bottom face of the insulator body. The recessing of the bottom cup serves to keep the hot bottom cup of a vapor dispenser removed from the vaporizer body from burning and melting items and surfaces it is place on.

Some aspects of exemplary implementations of portable aromatherapy vaporizers include a generally hollow cylindrical body with an open bottom, a bottom edge and an open top; a furnace with a heating element inside the furnace; a connection interface gasket providing a fluid pathway from the open top to the furnace; a chassis having a top and a bottom affixed within the body; a PCB (board) with a controller and battery supply affixed to the chassis; a temperature sensor in thermal communication with the furnace and in signal communication with the PCB; an on/off switch on the body's exterior in signal communication with the PCB; a recess formed near the bottom edge defined by the chassis bottom affixed above the bottom edge; and, wherein the recess forms a receptacle which is used to mate and accessory module. In some instances an accessory module which reversibly mates with the body at the recess.

Some aspects of exemplary implementations of portable aromatherapy vaporizers include a generally hollow cylindrical body with an open bottom, a bottom edge and an open top; a furnace with a heating element inside the furnace; a connection interface gasket providing a fluid pathway from the open top to the furnace; a chassis having a top and a bottom affixed within the body; a PCB (board) with a controller and battery supply affixed to the chassis; a temperature sensor in thermal communication with the furnace and in signal communication with the PCB; an on/off switch on the body's exterior in signal communication with the PCB; a recess formed near the bottom edge defined by the chassis bottom affixed above the bottom edge; and, wherein the recess forms a receptacle which is used to mate and accessory module. In some instances an accessory module which reversibly mates with the body at the recess. The chassis further includes a bottom face which contains at least one of an interface display, a power data/power interface, data input, power jack, each in signal communications with the PCB.

Some aspects of exemplary implementations of portable aromatherapy vaporizers include a generally hollow cylindrical body with an open bottom, a bottom edge and an open top; a furnace with a heating element inside the furnace; a connection interface gasket providing a fluid pathway from the open top to the furnace; a removable vapor dispenser which mates with the connection interface gasket; a chassis having a top and a bottom affixed within the body; a PCB (board) with a controller and battery supply affixed to the chassis; a temperature sensor in thermal communication with the furnace and in signal communication with the PCB; an on/off switch on the body's exterior in signal communication with the PCB; a recess formed near the bottom edge defined by the chassis bottom affixed above the bottom edge; and, wherein the recess forms a receptacle which is used to mate and accessory module. In some instances an accessory module which reversibly mates with the body at the recess. The chassis further includes a bottom face which contains at least one of an interface display, a power data/power interface, data input, power jack, each in signal communications with the PCB. In some instances the vapor dispenser includes an insulator body which holds a shaped container having an exit port and a bottom cup together forming removable material chamber. The vapor dispenser configured to removably mate with the body via the connection interface gasket. In some instances the open top is a first diameter and the open bottom is a second diameter, the first diameter being smaller than the second diameter. In some instances wherein the on/off switch is in signal communication with the control board and the control board controls the heating of the heating element based on input from the temperature sensor.

Aspects of the above portable aromatherapy vaporizer during operation provide heated air within A furnace which fills an air buffer region and collects until a pressure differential applied to a fluid pathway by one of inhalation or a fan causes the heated air to move into the material chamber through material thereby producing vapor and heated air.

Some aspects of exemplary implementations methods of portable aromatherapy vaporization include a method of ameliorating smell associated with vaporizing organic material by way of a sealable generally odor impervious accessory module reversibly mounted to a vaporizer body. The body contains heated air producing system fluidly connected to a vapor dispenser. A controller in signal communication with the heat producing system to control the temperature of the heat air and there is a means to mount the accessory module to the body. The accessory module is large enough to contain the vapor dispenser and whereby any smell associated with vaporized materials on the vapor dispenser are reduced by virtue of sealing the vapor dispenser in the accessory module.

The following description of examples of implementations, reference is made to the accompanying drawings that form a part hereof, and which show, by way of illustration, specific implementations of the present disclosure that may be utilized. Other implementations may be utilized and structural changes may be made without departing from the scope of the present disclosure.

FIGURES

The invention may be better understood by referring to the following figures. The components in the figures are not necessarily to scale, emphasis instead being placed upon illustrating the principles of the invention. In the figures, like reference numerals designate corresponding parts throughout the different views.

FIGS. 1A-1C illustrates aspects of a convection vaporizer with rotatable material chamber and fluid pathway;

FIGS. 3A-3C illustrate aspects of a furnaces with interfaces for supplying heated air in a convection vaporizer;

FIG. 3D illustrate aspects of a multi heating element furnace with interfaces for supplying heated air in a convection vaporizer;

FIGS. 4A to 4D illustrate assembly and aspects of reusable and disposable fluid pathways and material chambers;

FIGS. 5A-5D illustrate aspects of the interface between furnaces and fluid flow to inhalation outlet;

FIG. 6A illustrates an alternative placement of a furnace in a body of the disclosed vaporizer;

FIGS. 6B-6C illustrate exterior ornamental view of a vaporizer with top cover and bottom;

FIGS. 8A-8C illustrate a concentrating vaporizer with integral compartment storage;

FIGS. 9A and 9B illustrates exterior views of a cylindrical vaporizer with modular storage;

FIGS. 9C and 9D illustrate a vaporizer with compartment storage and heat recirculation;

FIG. 9E illustrates aspects of a vapor dispenser with recessed material chamber;

FIG. 10 illustrates aspects of another a vapor dispenser;

FIG. 11 illustrates a module accessory container with threaded mating to the body;

FIG. 12 illustrates a module accessory container module and body wherein the accessory has a mounting recess;

FIG. 13 illustrates a magnetic connection between accessory module and body;

FIGS. 14A and 14B illustrate another convection vaporizer with removable chamber and fluid pathway; and, FIG. 15 illustrates another convection vaporizer with modular removable storage.

Figure 2A:
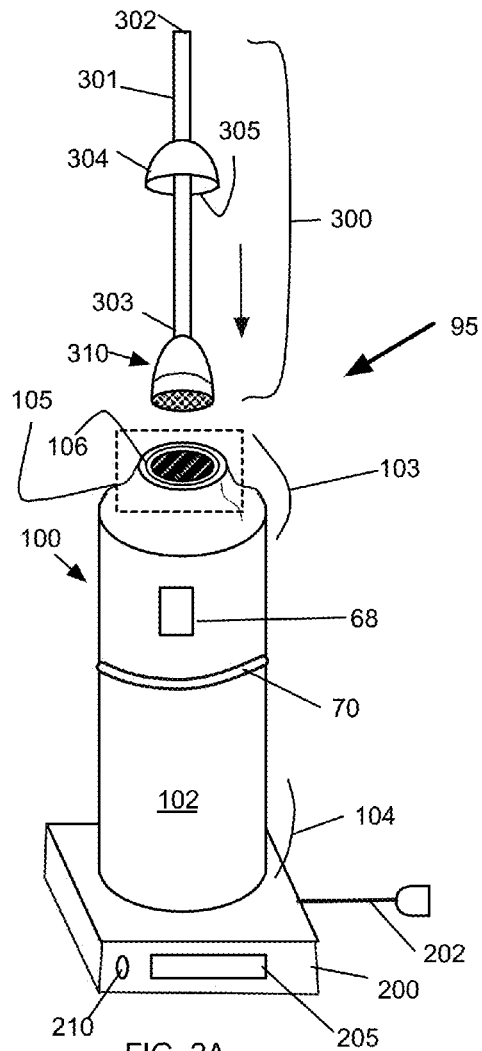
FIGS. 2A-2D illustrate aspects of convection vaporizer.
Figure 2B:
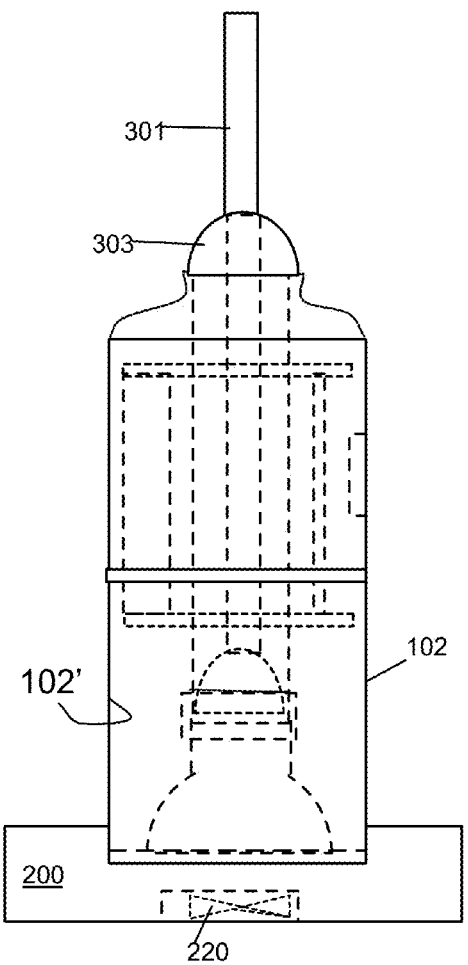
Figure 2C:
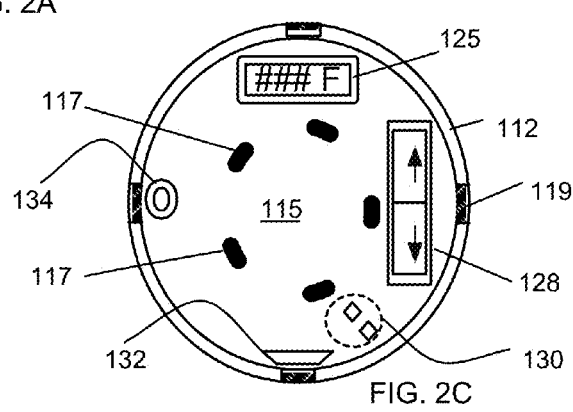
Figure 2D:
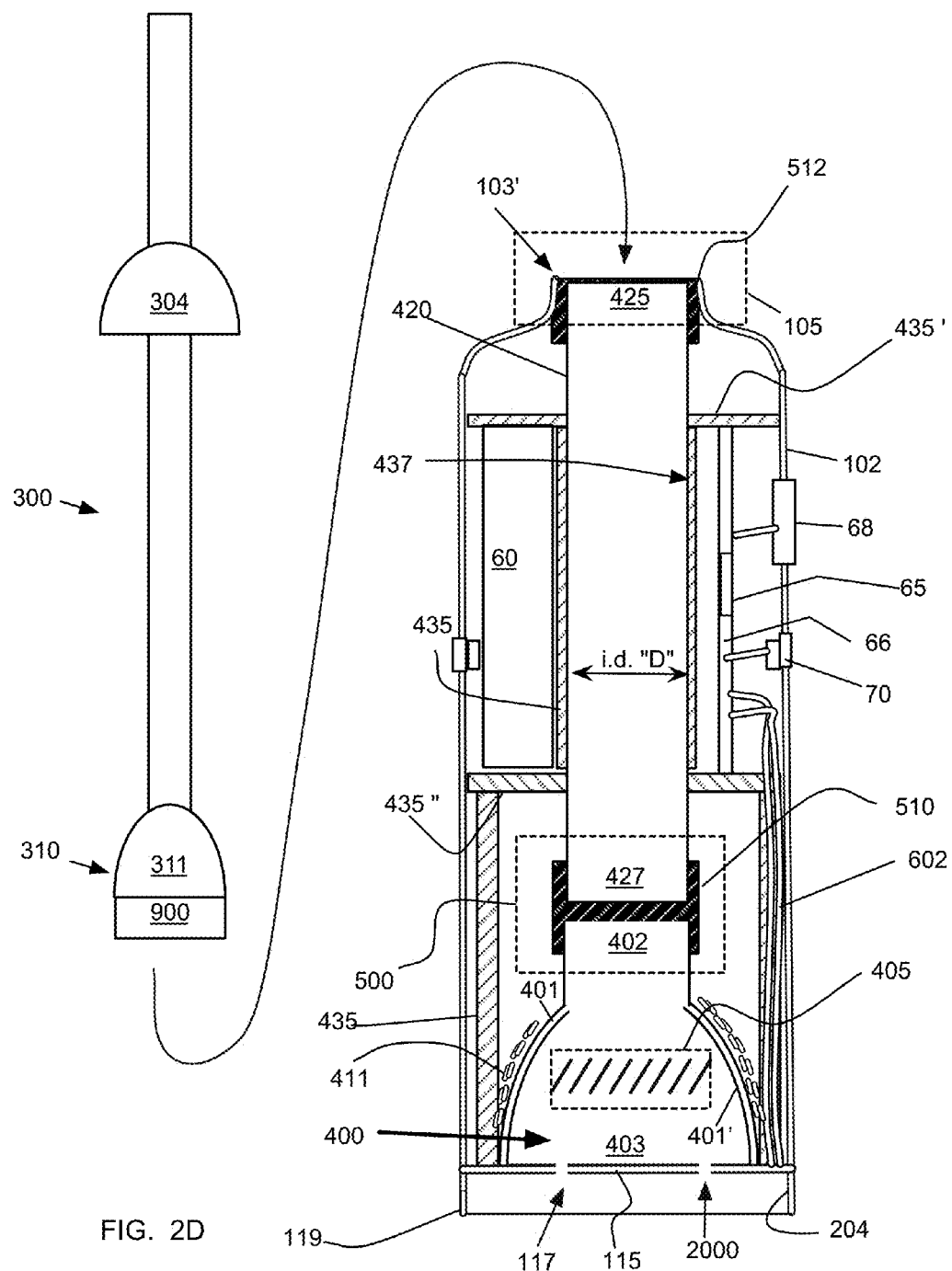

All descriptions and callouts in the Figures and all content therein are hereby incorporated by this reference as if fully set forth herein.

FURTHER DESCRIPTION

Disclosed herein are aspects, exemplary implementations and embodiments of aromatherapy vaporizers. In some instances the device and system is rechargeable with a battery power supply and is recharged on one of a base and a plug-in. The device can be disassociated from the base or power supply cable (plug-in) for use via the internal battery power supply. In some instances the device and system the pathway for the generation and use of vapor is a self contained module which is thermally and physically removable from the furnace and body of the device. Vapor residue and the odor associated therewith accumulate in the vapor fluid pathway. In some instances the vapor fluid pathway is relegated to a disposable chamber and exit fluid path. By confining the vapor pathway and material containment chamber to a removable (reusable) structure odor may be contained in that removable element which may be one or more of cleaned and stored in an odor reducing, or generally impervious chamber. By disposing of the vapor pathway and material containment chamber odor is eliminated and or reduced. In some instances the chamber containing the material to vaporize may be reusable and the exit fluid pathway may be disposable.

Disclosed aspects of the furnace include the more preferred use of a very thin wall to limit or reduce parasitic thermal losses due to thermal mass. Alternatively, a ceramic furnace may be used.

Furnace bodies with concentrator shape force a rising volume of heated air into a smaller volume thereby facilitating a chimney effect and causing convection which may be used to fill a container and/or cause aroma to exit the device without inhalation or fans.

Furnace bodies with buffer regions above the heating coil(s) have been tested and improve heat management and delivery wherein pre-heated air may be positioned in the buffer region below the material containing chamber. Said preheated air has limited penetration into the material without a negative pressure above same.

Vaporizing plant material or extracts for inhalation of compounds therefrom is considered by some to be less harmful then combusting the same plant material.

In a traditional vaporization system the fluid pathway and material chamber will become sticky and coated with residues. The resulting adhesions cause smell and may reduce function.

Aspects of vaporizers, systems and methods of use involving utilizing temperature controlled heated air to release organic compounds from plant materials and extracts is disclosed. In some instances the furnace characteristics reduce power requirements for heating and/or reduce the parasitic heat losses.

In some instances the control system includes one or more of software, logic, sensors, LEDs, thermistors, thermocouples and controllers having hardware, memory and microprocessors to one or more of control, limit, warn about or prevent over heating of materials. In some instance the vaporizer includes wife, Bluetooth or other wireless communication to a smart phone to allow an application on the smart phone to control heating parameters and/or monitor usage and performance. In some instance the vaporizer includes Wi-Fi, Bluetooth or other wireless communication to allow an application on the units base (which optionally may have a processor), computer, streaming box or smart phone to control temperature settings.

The instant disclosure teaches aspects of vaporizers utilizing heated air flow (convection) via a shaped concentrating furnace to efficiently heat material (which includes one or more of concentrate, extract and plant material) in at least one of a disposable and a removable chamber and fluid pathway for exit.

The instant disclosure teaches aspects of vaporizers utilizing heated air flow (convection) via a shaped concentrating furnace to efficiently heat material (which includes one or more of concentrate, extract and plant material) in at least one of a reusable and a removable chamber and fluid pathway for exit.

FIGS. 1A-1B illustrates a vaporizer 10 with a rotating multi-zone chamber 11. The body 12 is generally hollow with a closed bottom 13 and an open top 14 with a first rotating interface 15 which mates with the bottom 16 of the chamber. The air intake 17 is at the bottom of the manifold. The open top of the chamber 18 opens to the chamber cavity 19 which has an open bottom having a floor 20 which is permeable to vapor and heated air. The manifold 30 has an open top 32 which is shaped to less than the chamber size, shown in FIG. 1B is a ⅓ the size of a chamber floor sized manifold open top 32. An inhalation top 34 fits over the chamber at its open bottom 35 and inhalation is via the exit of the inhalation fluid pathway which 40. One or more baffles 42 may be placed in the fluid flow pathway to direct fluid flow. FIG. 1B a view along the line of "A"-"A" of FIG. 1A. FIG. 1C is a view along the line of FIG. 1A.

During use the manifold open top 32 provides heat to the chamber via the chamber floor. The shaped manifold top provides heat to a section "X" (and any associated material) of the chamber. FIG. 1C shows section "X" aligned with open manifold top 32. During inhalation the non-heated air 2000 travels in the intake 17 then through the manifold 30 and out the shaped top of the manifold 32 through the floor of the chamber 20 and through section "X" and any material therein, thereby releasing the vapor (not shown) which travels through the inhalation top 34 and baffle 42 cooling the vapor to form cooler vapor 2175 and exiting through the inhalation fluid exit 40. Upon rotation along the line of arrow 1500 a user can turn the rotating chamber and attached top 34 to move to the next section ("Y" or "Z").

Power to a heating element 50 within the manifold is provided by a portable power supply 60 such as lithium ion batteries. A controller 65 associated with a printed circuit board (PCB) 66 controls the power supplied to the heating element. An on/off switch 68 is in signal communication with the PCB. A communication means 70 such as a light, LED, lens dispersing an led and the like is visible from the exterior of the case. An I/O (input/output) 80 such as any variation of a universal serial bus (USB) or a wireless communication. Additionally, a power adapter plug in 84 may be provided to recharge internal batteries. The USB, in some instance, may also be used to recharge. The I/O may be used for data communication with the PCB and controller and/or recharge of the battery. A WI-FI® enabled chip 84 such as 802.11 protocol may be provided for communication with the controller 65 and the PCB 66. A temperature sensor 90 such as a thermistor or thermocouple may be placed in thermal communication with the interior or exterior of the manifold and is in signal communication with the controller and PCB. An airflow sensor 92 may also be in signal communication with the controller and PCB.

In FIGS. 2A-2D show overviews of some aspects of main components of a concentrating convection vaporizer system 95. A vessel 100 forms the base of the vaporizer. The external body 102 forms a vessel which is a substantially hollow shroud/cover, the body has a top region 103, with a top opening 103' which forms a fluid connection from the exterior of the device to the interior. The fluid connect may be to a furnace directly or connects to a duct 420. The body has a bottom region 104 and a bottom edge 204. A to duct interface 105 formed at the top region 103 provides a fluid connection from the exterior of the vessel through the opening 103' to the interior 102' of the body 102 into a duct 420. An on/off switch 68 that may be a touch switch, contact or pressure switch is user accessible from the exterior of the body 102. The switch may be push on push off, the switch may be programmable, or controlled by the control board wherein activation causes the device to enter a steady on state to continually heat botanicals for aromatherapy over a preselected period of time. One or more communications illumination means 70 are provided attached to or illuminating through lens, apertures and the like in the body to be visible from the exterior of the body. The illumination means includes but is not limited to one or more lenses, LEDs (light emitting diode), electroluminescent band, and may be a series of drilled holes or very thin body areas that an illumination from the LEDs able to penetrate there through. The vessel 100 is shown removable connected to a charging base 200 and a removable fluid pathway 300 (including a material chamber 310 which may be multipart) fits into the top duct interface 105 to form the fluid path for both heated air and vapor liberated from material. Those of ordinary skill in the art will recognize that a non-removable fluid pathway is within the scope of this disclosure and a chamber with an affixed or non-removable fluid pathway (NRFP) is within the scope. Colored illumination such as light emitting diodes (LEDS) are useful for communications. An illumination visual language is used wherein the one or more printed circuit boards (PCB) "board" 66 with a controller 65, memory and other components to support signal communication and input/output to control functions of the device. PCBs and controllers are well known in the art. Pulse width modulation (PWM) power management, temperature sensor inputs, memory, clock, and Wi-Fi connect ability are a non-exclusive list of PCB "board" components and functions. all be control one or more of color, strobe, frequency, intensity and movement (by turning some LEDs off in the band of lighting) of illumination to convey state of the device. For example green may mean at temperature and ready to use. Red may mean heating up. Flashing red may mean time to recharge. Blue may mean standby mode.

At the bottom 112 of the body is an inserted, affixed or otherwise attached closure or floor 115 which also may be a part of an internal chassis 435. One or more air intakes 117 may be formed on that closure to provide a fluid passage for external air to be drawn into the vessel during heating and use. Intake vents 119 may also be added to allow air flow through the side edge of the body.

User interface display 125 and inputs 128, recharge to base connectors 130, data/power interface 132 and/or power jack 134 are shown on the bottom closure or floor 115.

Inside the body 102' is the heart of the control system and heating systems. The substantially hollow furnace 400 has a thin wall 401 with an interior surface 401' forming a container which allows for intake of external air and for air heated therein to exit. In this exemplar the furnace has a narrower diameter open top 402 and a wider diameter bottom 403. Preferably the wall is less than 1 millimeter thick, more preferably less than 0.5 millimeters thick and most preferably less than 0.25 millimeters thick. Suitable materials should have no harmful levels of outgassing at temperatures the furnace will be used at. These materials include but are not limited to phenolic resins, aluminum, titanium, stainless steel, and ceramic. A heating element 405 such as a kanthal or nichrome coiled wire is within the furnace. Optionally insulation 411 may wrap at least some of the thin wall of the furnace. The gasket 500 fluidly connecting the chamber and, also known as the chamber gasket interface (CGI) forms a portion of a guide pathway whereby the material chamber 310 mates with the furnace. That gasket 500 may be at the region between the duct and furnace or directly between the furnace and a top mounted chamber. The illustrated duct 420 has an internal diameter (i.d.) denoted by "D". The duct has an open top or proximal end 425 and an open bottom or distal end 427. To connect the duct to the furnace the distal end 427 is brought near the open top 402 of the furnace via an insulation member 510.

The insulation member may be a pliable or semi pliable gasket, silicon tape, molded ring, ceramic, polyimide film or the like and it functions to hold the duct and furnace ends aligned while separating the two ends to limit heat transfer, parasitic losses due to heat transfer. Further the insulating member may be formed to hold and isolate the inserted removable fluid pathway 300 from thermal contact with the duct (see FIG. 5B). To connect the duct to the body 102 at the gasket 500, the insulation member 510 may have an interface gasket 514 (see FIG. 5A). The interface gasket connects the exterior of the body near the top section 103 and the exterior of the top 425 of the duct. The band 515 may be used to separate the duct and the body from direct physical contact and to limit thermal contact via the insulating properties of the insulation member 510. The band has an internal diameter "Di" which is less than the internal diameter "D" of the duct. At least the band is compressible. The insulation member is preferably compressible. The band (515) may be a homogeneous thickness or it may be non-homogeneous having thicker portions (516) laving spaces between the edge of the chamber and the band. The band or band and insulation member combination should be sufficiently compressible to allow the press fit of the chamber into the band whereby the chamber s held inside the duct without touching the duct wall.

The vessel 100 contains a power supply such as lithium ion batteries 400 and it can be charged with one or more of the recharge to base connectors 130, data/power interface 132 and/or power jack 134. Accordingly, it may be charged on or off the base.

The removable fluid pathway 300 provides a substantially hollow flow channel 301 and an outlet 302 and an inlet 303 connected to the material chamber 310. Optionally a spacer 304 may be fitted to the exterior of the flow channel to one or more of act as a heat exchanger to the flow channel, position the fluid pathway 300 within the duct 420, provide a grab for a user to remove the fluid pathway 300.

A heating element 405 such as a stainless steel, kanthal or nichrome coiled wire is fixed within the furnace. Optionally insulation 411 may wrap at least some of the thin wall. The duct 420 spans from the point heated air exits the open top 402 of the furnace to the touches the material in the material chamber 310, then through the flow channel to below the outlet 302. In practice the bottom edge 305 of the spacer 304 can be fit into a guide 106 around the top duct interface 105 to assist with positing and spacing of the chamber of material in the duct above the furnace.

A chassis 435 is a preferred means to space the duct in an aligned position with the furnace. It can hold circuit boards, batteries and support connections and illumination components. However, those of ordinary skill in the art will recognize that the chassis may be eliminated in the power and control elements placed in a casing without departing from the scope of the disclosure. The chassis 435 shown has a chassis top 435' and a chassis bottom 435" extended radial wall to position it within the body. In some instances the chassis is below the furnace. In some instances it fits around a duct and is placed above the furnace. If placed above the furnace a central core 437 of the chassis fits around the duct and may be solid, segmented, a series of studs with air gaps or any configuration which allows insertion of the fluid pathway. The battery power supply 60 and the control board(s) which contains the electrical components to manage temperature, adjust power, activate and change the output of the communication illumination, receive instructions from an app, it may support the pulse width modulation sensor inputs and battery charge discharge control. It may contain a 802.11 chip for wireless data exchanges and support wired data connections as well or other user interface. The board 66 may be one or more printed circuit board(s) PCB and the like and is also affixed to the chassis 435. Some connection wires 602 from the heating element to the PCB are shown. The other electrical switches and sensors are also connected to the control board(s). The control board(s) are in signal communications with electrical components of the vaporizer, including but not limited to temperature sensor(s), battery, illumination, on/off switch, charging board, display(s), user interface, input/output and applications that may be sued to communicate with the control board(s).

FIGS. 2A-3D show more aspects of a furnace 400 and the gasket 500. The furnace has both an inner surface 401' and an outer surface 401". One or both of the surfaces may be coated, anodized, electroplated, laminated and/or otherwise adhered or fixed to another material. Optionally a fluidly connected divider also known as an air permeably element 410 which is generally thin, conductive, and with perforations or holes to allow air passage may be fitted into the open top 402 below the top circumferential rim 412. The permeable element may be a metal disk with drilled or laser etched holes. Depending on the usage and how much heat is to be stored in the fluidly connected divider 410, the fluidly connected divider 410 may be very thin (thousandths of an inch) or thicker. A thicker metal (or conductive) fluidly connected divider 410 will act as a heat sink which can be used to provide radiation and conduction of heat a chamber of material inserted in the open top 402 in addition to the heated convection air flow.

The heating element 405 has leads 406 extending therefrom for connection to the PCB 66 and/or battery 60 power supply.

Non-heated air 2000 enters one or more air intakes 117 which provide a fluid passage for such air to be passed into the furnace 400. Alternatively, if a high-efficiency particulate air (HEPA) filter 415 or other air filter is added to the fluid pathway of the air, it should be at the upstream leg of the journey. Air intakes 417 to the HEPA 415 provide a pathway for the air through the filter material 416 (which removes containments) then into the furnace via the intakes 117.

The electrical heating element 405 is heated with power from the battery power supply 60 and the action of the heating element is adjusted via the controller 65 which receives sensor data from at least one temperature sensor 90 such as a thermistor or other thermocouple. The temperature sensor(s) 90 may be placed inside the furnace and/or outside the furnace. The control board contains a microprocessor, memory and software which may include look up tables and may have pulse width modulation functionality. The control board processes the sensor data and adjusts power to the heating element to achieve a predetermined or pre-set, or selected temperature of air at or near the interface 500.

The air passing through the furnace and over the heating element carries heat forming heated air 2150 and as the heated air 2150 rises in the furnace toward the open top. FIGS. 3A and 3B the air rises into a reduced volume space and the flow is accelerated as it passes through the gasket 500 (which may also be a thermal insulator) and passes thorough material "M" forming the vaporization air flow (VAF) 2175. The increase in hot air movement or flow from the concentration of the rising heated air also may be used to cause convection air flow through the device without a fan.

FIGS. 3C and 3D illustrates a furnace 400 with a heat buffer zone 4000. In one exemplar a single heating element 405 receives power from the battery via the controller and heats the unheated air "HA" which fills the furnace up as the heated air 2150. In another implementation a second heating element 405' independently controlled by the controller 65 is illustrated.

The furnace forms part of a heat management system which includes, moving from bottom to top, a floor 115 with vents 117. The vented floor partially seals off the bottom region 408 of the furnace 400. Within the bottom region of the furnace is the at least one heating element 405. As noted above a second separately controlled heating element 405' may be added. Above the heating element is a volume of space in the upper furnace 409 which forms a temperature buffer 4000. The temperature buffer 4000 is between the heating element(s) and the fluidly connected divider 410.

The temperature buffer 4000 temporarily contains heated air within a preferably insulated furnace. The stored air is used to limit lag time from when the heating element is powered on to when it can deliver heated air at a desired temperature. Material "M" in a chamber 310 above the fluidly connected divider 410 also blocks the perforations in the fluidly connected divider limiting the movement of heated air into the material "M". Accordingly, a volume of heated air is staged to be drawn into the material "M". A fluid pathway (RFP) 300 fluidly connected to the chamber 310 may be used to accomplish same. The chamber 310 is fluidly connected to the furnace 400 by way of the CIG 500. A more detailed description of the interface is provided below concerning aspects of the implementations shown in FIGS. 5A-5C, 8A and 9C.

The fluidly connected divider 410 is below the chamber 310. The heated air in the temperature buffer absent negative pressure above or positive pressure below does not readily move into the chamber and material "M" via said fluidly connected divider 410. Rather the fluidly connected divider 410 and material M cooperate to limit heated airflow absent said pressure differential. The limit to heated air movement act as a pressure regulated air damn which allows the device and method to form a region of heated air 2150 which may be delivered via a pressure differential. In practical terms a user during an inhalation will cause a negative pressure above the chamber and draw the heated air from the temperature buffer area 4000 into the chamber and material "M" thereby causing essential oils and resins, Terpenes and other volatile compounds to be liberated into vapor. A temperature sensor 90 inside or outside the furnace in signal communication with the PCB and controller 65 thereon provides temperature data whereby the controller 65 adjusts power requirements to maintain a target temperature of the relatively still heated air when the pressure is constant and the air which is flowing at an accelerated rate due to inhalation or a fan causing a pressure differential.

FIGS. 4A-4D illustrate aspects of removable fluid pathway (RFP) 300 connected to a chamber 310 either or both of which are removable from the chamber interface gasket 500. The RFP 300 and material chamber 310 span from the point heated air touches the material to the point the vaporized material is expelled into a space (aromatherapy) or inhaled. The RFP, optionally has a spacer 304 as previously discussed. A RFP and chamber can be configured to assemble and disassemble for fill, cleaning and refill or the combination may be fixed and non-refillable or disposable. The RFP may be reusable and the material chamber 310 reusable. The RFP may be reusable and the material chamber disposable. The RFP may be disposable and the material chamber 310 reusable. The RFP may be disposable and the material chamber 310 or portions thereof disposable.

Figure 4A:
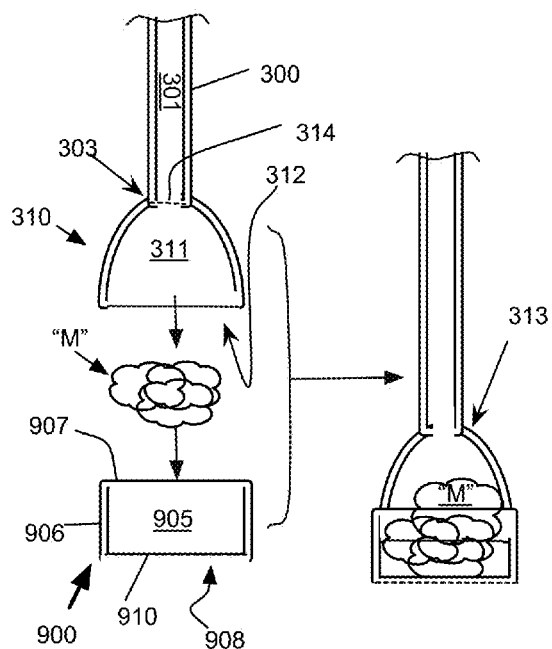

FIG. 4A shows aspects of assembly of a material chamber 310. The chamber has a shaped container 311 and an open cup 900. The shaped container 311 is generally hollow with an open bottom 312 and a partially sealed top 313. A screen 314 or mesh material to allow airflow but restrict any particulate from ascending the RFP may be added in the fluid path exiting the partially sealed top. The chamber is connected to the inlet 303 of the removable fluid pathway 300. Material 800 for vaporization is added to the cylindrical chamber bottom cup 900 which is used as a sealing cap or member. The chamber floor has an internal cavity 905, formed by an annular wall 906 with an interior surface and an exterior surface and having an open top 907 to receive the open bottom 312 of the chamber of the shaped container 311 and an open 908 bottom which receives an air permeable element 910 such as a screen. Material "M" to vaporize is placed in the bottom cup 900 and when the heated air 2150 (shown in FIG. 5B) interacts with the material "M" it heats the material until compounds in the material are released via vaporization and the VAF, without combustion, rises for aromatherapy.

The bottom cup 900 is one of connected to the shaped chamber 311 either permanently or reversibly. Method of connection include but are not limited to latch and catch, snapping, screwing, pressure fit, and friction fit. The annular wall 906 may be further modified or formed to be threaded to receive the open bottom 312 via rotation. Those of ordinary skill in the art will recognize that the annular wall and screen may be formed as one part of stamping, molding wherein air passage holes are laser drilled, drilled or punched through such a unitary chamber floor.

Figure 4C:
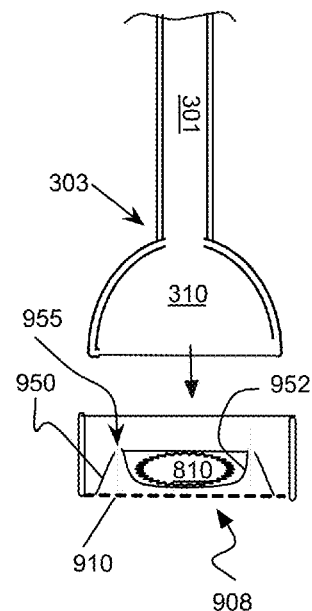
Figure 4B:
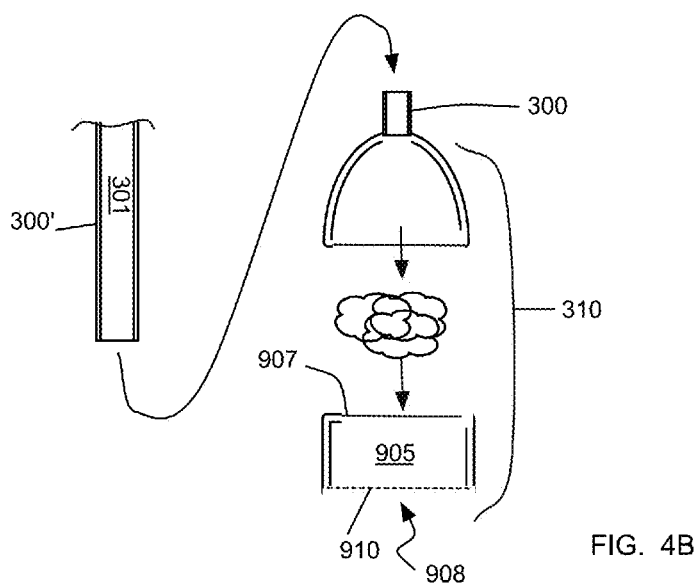

In FIG. 4B an inhaler tube 300' slips over the fluid pathway 300 thereby extending the fluid pathway. That inhaler tube may be disposable such as paper or plastic. if may be silicone or plastic tubing, it may be reusable such as ceramic, steel, aluminum and plastics. Method of connection include but are not limited to latch and catch, snapping, screwing, pressure fit, adhesive, and friction fit.

In FIG. 4C an extract or oil tray 950 is added to the bottom cup 900, the tray has a bowl region 952 and may have air vents 955. When utilized for aromatherapy a heated airflow rises from the furnace passes to the fluidly connected chamber and around the tray thereby heating the tray to a desired temperature causing the extract 810 to release vapor.

In FIG. 4D a simplified chamber assembly 310A is shown. The shaped chamber 311P contains one of material "M" and extract 810. The chamber has a chamber floor 901 is snapped or press fit into the shaped chamber 311P such as pressing a metal screen therein attached thereto and it has an air permeable region 910. The air permeable region may be formed as part of the floor 901. A airtight seal 975 such as plastic or foil, coated paper or mylar may be adhered to the chamber to seal it with a second seal 975 sealing the RFP. Sealing is not required but optional. Alternatively the RFP and chamber may be vacuum sealed in a plastic wrapper/bag 977. Section 980 of the shaped chamber is preferably vertical to support insertion into the band 515 and compression thereof.

FIGS. 5A-5D illustrate the isolation of the RFP and chamber in the chamber interface gasket 500. The insulation member 510 forms a connection between the furnace and duct (as discussed above). The member 510 has an outer annular wall 512 an inner annular wall 513 and is generally hollow. It is however partial bisected by an isolation band 515. The isolation band may be used to one or more of physically and thermally separate the duct 420 and the open top 402 of the furnace. The band 515 extends from the inner annular wall 514 towards the center of the member 510. When connected to the duct's distal end 427 the band 515 reduces the diameter of the passage formed there through to less than the i.d. "D" of the duct. The isolation interface 2500 is the area wherein the band is used to pairing a chamber with floor having a cross sectional maximum diameter less than the i.d. "D" of the duct with the duct a user inserts the RFP into the duct 420. The chamber In those instances where the floor forms the outermost region of the chamber the exterior of the floor 906 is the portion that compresses the band 515 and bottom cup 900 assembly passes into the CIG 500 and the is isolated by the insulating member 510 at the band 515 wherein the chamber 310 is positioned remote from the inner wall of the duct. Shown in FIG. 5D is the furnace 400 with an air buffer region 4000 as described above in reference to FIGS. 3C and 3D. After the heated air 2150 passes through the material "M" the VAF 2175 cools 2185 as it passes through the RFP or a non-removable fluid pathway NRFP.

Once the chamber attached to the fluid pathway mates to the system at the isolation interface 2500, heated air 2150 from the furnace may be drawn (via a pressure differential) through material (or heat the extract) and organic compounds vaporize as heated air of the correct temperature interacts with same. The vapor and heated air 2175 passes into the flow channel 301. The vapor and heated air 2175 cool 2185 during passage through the length of the fluid pathway in the flow channel.

FIG. 6A illustrates a vaporizer with a furnace 400 and side wall air intakes 3000. In this alternative the chamber mates directly into the open top 402 of the furnace thereby eliminating the duct.

FIG. 6B illustrates a vaporizer with a furnace 400 having an on/off switch 68 and an illumination communication means. In this illustration the design is a cylindrical body 12B closed off with a cylindrical end cover 3050. The bottom 115B is circular (FIG. 6C).

Figure 7:
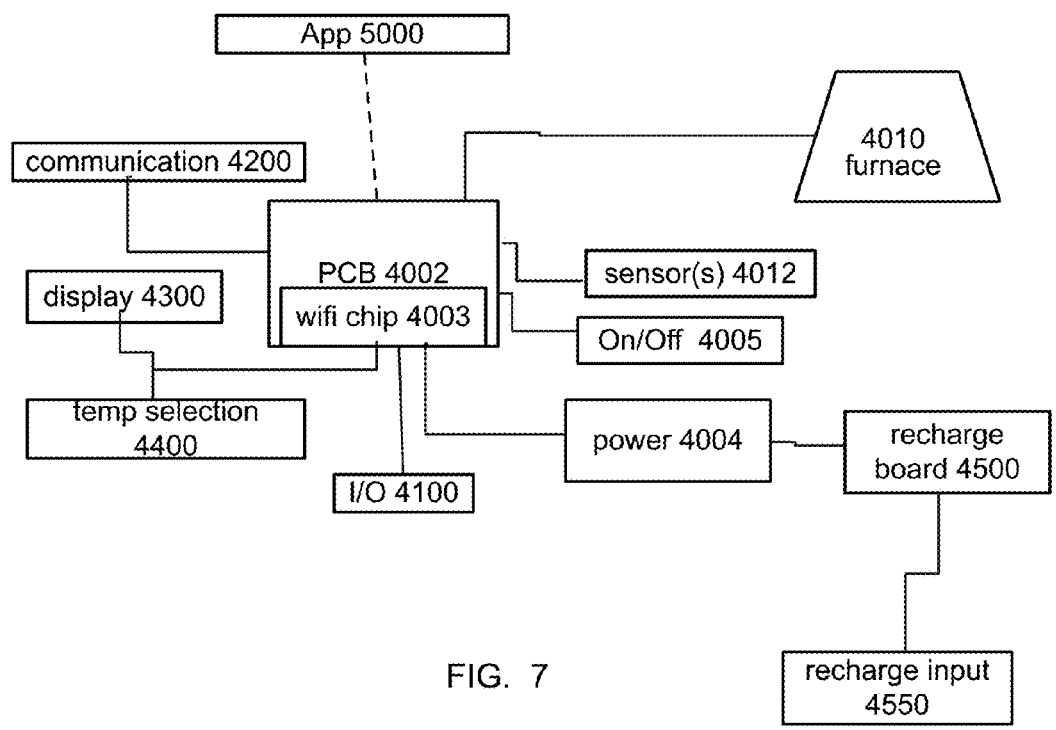
FIG. 7 illustrates aspects of major electrical components of a vaporizer.

FIG. 7 shows aspects of main components of the control, electrical and heating systems of an exemplary implementation of a vaporizer device. A printed circuit board(s) (PCB) 4002 contains memory, processors and the circuit components to control heating and communications including pulse width modulation and inputs for sensors. The board is also electrically or wirelessly in signal communication with, and/or connected to:

1. A power supply 4004 which may be battery or the onboard battery may be exchanged for a plug in variation to supply power from a remote battery supply, plug in the wall supply or other electrical power generator. If the battery is on board the device a board to manage recharge 4500 is connected to the battery supply and an input to recharge 4550.

2. A furnace 4010 with at least one heating element therein.

3. One or more sensors 4012 to monitor, report and provide data to the PCB to control temperature of the system.

4. One or more on/off switches 4005.

5. One or more inputs and outputs for data transfer, and/or charging.

6. A communications output 4200 such as LEDs to provide illumination information which relates to device operation.

7. A display 4300 (which may also be combined with the communications output 4200) and temperature selection 4400 which is a user interface to set a desired VAF temperature.

8. An application 5000 on a computing device or smart phone which communicates wirelessly or through a wired connection (I/O) to adjust temperature, control operation and report operation and usage.

9. Wi-Fi chip such as 802.11xx chip.

FIGS. 8A-15 illustrate aspects of implementations of aromatherapy vaporizers and aspects of modular encasements 6010 attachable to said vaporizer. A safer material chamber module provides vapor dispensing function is also disclosed. Finally, heat exchange system to leverage the air heated in the air insulation zone (AIZ) of a vaporizer and thus both reduce case heating and reduce energy needed to heat the incoming air is disclosed.

In FIGS. 8A-15 overviews, in some instances convection vaporizer may include removable storage to ameliorate smell associated with vaporizing material including smell or odor of resins and oils which may coat portions of the material chamber and fluid pathway, by storing the chamber, fluid pathway, to avoid loss of parts or disassociation and/or store items.

FIG. 8A is an assembly view of a convection vaporizer with modular storage.

An external body 6002 forms the base of the vaporizer that is substantially hollow, the body has a top region 103 which is a first diameter and said first diameter is smaller than the second diameter of the bottom 6008. that provides a fluid connection from the exterior of the vessel through the opening 103' to the interior of the body 6002. Inside the body is a substantially hollow furnace 400 has a thin wall with an interior surface 401'. Preferably the wall is less than 1 millimeter thick, more preferably less than 0.5 millimeters thick and most preferably less than 0.25 millimeters thick. Suitable materials should have no harmful levels of outgassing at temperatures the furnace will be used at. These materials include but are not limited to phenolic resins, aluminum, titanium, stainless steel, and ceramic. A heating element 405 such as a kanthal or nichrome coiled wire is within the furnace. In some instances ceramic heaters or High-temperature co-fired ceramics (HTCC) with metal element layered therein or thereon may be used in place of the coiled wire. Optionally, insulation 411 may wrap at least some of the thin wall of the furnace. A floor 115' is shown substantially closing off the wider base 403 of the furnace. Air intakes 117 are formed through that floor. The floor is constructive of a material that does not outgas at the temperature it is exposed to during aromatherapy vaporization. A non exclusive list of suitable materials include borosilicate, ceramic, stainless steel, aluminum, ABS, phenolic resins and the like. The furnace may be shaped with a wider diameter base than top portion. The shape will facilitate accelerated airflow as heated air is concentrated due to space/volume reduction in the upper portions of the furnace.

Within the body a chassis 435 with a top 435' a bottom 435" and one or more internal support posts 436 is shown. The chassis can support the PCB "board" 66 and battery supply 700. Near the bottom region 6008 of the body 6002 is a recess 6009 of the body above the bottom edge 204, the bottom 435" of the chassis is fixed into the body and may be sealed to form a barrier to seal off an attached module 6010. The bottom of the chassis recess 6009 which forms a receptacle which is used to attached, mount, mate, connect, catches or otherwise latch a mounting of the accessory module 6010 thereon. On the bottom face 437 of the chassis 435" a user interface display 125, a power data/power interface 132 and inputs 128. A separate power jack 134 may be formed through the body. Each being in signal communications with the circuitry on the PCB board. Those of ordinary kill in the art will understand that a separate end closure (not shown) portion may be added near the bottom recess 6009 of the body below the bottom face and that addition is within the scope if this disclosure.

In some instance an optional fan 3002 may be placed in the body between the chassis and the floor 115'. The device and fan, in this exemplar, has one or more air intakes 3003 to intake air from outside the body via one or more vents in the body 3000. Optionally an airflow sensor 92 may be placed within the airflow. The airflow sensor measures the change in airflow and is in signal communication with the controller 65 on the PCB. The controller may use airflow measurement as one variable to adjust the electricity being supplied to the heating element. The controller has additional inputs including the on/off switch and the temperature sensor. One or more look up tables in memory on the PCB may also be used when the controller adjusts temperature by regulating the electricity flow to the heating element. Pulse width modulation (PWM) is one scheme for adjusting said electricity flow.

Assembly of the device includes affixing the furnace 400 and chassis and associated boards and batteries into the body. Between the open top 402 of the furnace and the body's top region 103 is another variation of a Connection Interface Gasket (CIG) 9000 having upper interface "IFA" and a lower interface "IFB" separated by a Fluid Passage "FP". The CIG 9000 fits within the top region 103 and the lower interface "IFB" mates with the open top 402 of the furnace. The vaporizer body and associated heating, control and power elements once constructed reversibly mate with a herbal material (or extract) vapor dispenser 8000 which places, material over the furnace for aromatherapy vaporization.

The material for vaporization is confined in a material chamber 310 with a shaped container 311P which is preferably dome shaped and has a reduced size vapor exit port 315 which surround the fluid pathway 300, and which reversibly connects to a bottom cup 900. Aspects of the removable chamber/cartridge with fluid pathway generally called out as a vapor dispenser 8000 include providing an insulated and therefore cooler physical surface for a user to handle, providing a refillable chamber, and raising the air permeable bottom cup 900 bottom of the chamber away from the bottom face 8004 of the cooler surface. The raising of the chamber allows placement of a hot chamber on a surface wherein only the cooler bottom face 8004 is in physical contact with said surface. The vapor dispenser 8000 comprises an insulator body 8001 which further includes sub groupings of a base 8002 with a side wall 8006 (which may include divots or bumps to assist in gripping (not shown)), a bottom face 8004 and a mounting guide (or gap) 8008 whereby the vapor dispenser. During mounting the vapor dispenser mates with the upper interface "IFA" via the bottom cup 900 which fits into the upper portion of the gasket whereby the fluid path "FP" separates the furnace and chamber. A generally ridged tube 7000 with an inhalation end 7001 and a mounting end 7002 may be fitted over the exit port 315 to extend the fluid pathway for vapor. Alternatively a flexible hose-like tube 7010 with an inhalation end 7011 and a mounting end 7012 may be fitted over the exit port 315 to extend the vapor fluid pathway. The shaped container 311 and the bottom cup 900 and with exit port 315 form the material chamber 310. The material chamber 310 is removable from the insulator body 8001 by applying a downward force at the exit port 315 thereby dislodging the material chamber. The material chamber may be held via one or more magnets 6095 into the insulator body 8001. Other latch and catch alternatives are within the scope of this disclosure. Such members may include mating guides, a bump at the junction of the exit port 315 and the top of 8002 whereby when mounted the bump 316 (see FIG. 9E) temporarily holds the material chamber in the insulator body until it is pressed out. Those of ordinary skill in the art will recognize that there are many mechanical variations and magnetic variations to accomplish the release and affixation of the material chamber in the insulator body. All such variations are within the scope of these disclosure. A key features is that the material chamber is held within the insulator body thereby keeping the heated material chamber inside the insulator body. In this fashion if a vapor dispenser 8000 is placed on a surface ("S") the material chamber portion is kept remote from the surface thereby eliminating contact and reducing or eliminating burning, melting or heating of the surface it is placed on.

The furnace 400 is activated via an on/off switch 108A which may include a communication illumination means 110 formed at or near the on/off switch whereby the communication via light intensity, color, blink or flashing can advise a user of information such as state of the device. The optional fan 3002, if included, is activated via an on/off switch 108B which may include a communication illumination means formed at or near the on/off switch. The switches are in signal communication with the PCB.

The accessory module 6010 is a sealable container which reversibly mates with the body 6009. The body may have a bottom recess 6009. The module 6010 is cup shaped with a closed bottom 6011 and a generally hollow interior 6012. To access the interior of the module an open top 6014 is provided. An O-ring or other seal/gasket 6016 may be placed in or at the open top region 6020 as a seal to the body. Alternatively, a gasket or seal 6022 may be formed on the bottom face 437 to seal along the top edge of the open top 6014. Although not shown, the open top may be threaded and mate with a corresponding threading in the bottom region of the body.

In some instances the module 6010 may be sealed at its open top via a lid 6030 which fits into the open top. A gasket 6032 or O-ring) not shown) may be added to further seal off the module. The accessory module is a generally hollow container with an open top and closed bottom.

FIGS. 8B and 8C illustrate the module 6010 utilized to house the removable vapor dispenser 8000. In this fashion the method and system contains the removable vapor dispenser 8000 which may be associated with residue after aromatherapy use. The module reduces smell. The module also serves to prevent disassociation of parts and secure storage.

FIGS. 9A-9E illustrate aspects of aromatherapy vaporizers 6050 and aspects of accessory modules 6010 which connect/combine with said vaporizer.

FIGS. 9A to 9C shows the exterior of a cylindrical body 6002. The bottom of the body 6002 may be the same as the bottom shown in FIG. 6C. An on/off switch is affixed on the exterior of the body and is in signal communication with the PCB and controller. An accessory module 6010 is shown attached and the bottom of that accessory module 6010A is shown in FIG. 9B.

FIG. 9D to 9E illustrate the safer material chamber module formed as part of a vapor dispenser 8000. An optional heat exchange system to leverage the air heated in the air insulation zone (AIZ) of a vaporizer and thus both reduce case heating and reduce energy needed to heat the incoming air is disclosed.

Aspects of main components of the convection vaporizer system include an external body 6002 which forms the base of the vaporizer that is substantially hollow, the body has a top region 103, with a top opening which provides a fluid connection from the exterior of the vessel through to the interior of the body 6002. Inside the body is one of a tubular furnace 400 (see FIG. 8A) or a shaped furnace with a wider base 403 which allows for intake of air and for air heated therein to exit through its narrower diameter open top 402. Preferably the wall of the furnace is an insulator such as ceramic and about 2 to about 4 mm in thickness. If stainless steel is utilized the furnace wall is preferably less than 1 mm thick and more preferably less than 0.5 millimeters thick and most preferably less than 0.25 millimeters thick. Suitable materials should have no harmful levels of outgassing at temperatures the furnace will be used at. These materials include but are not limited to phenolic resins, aluminum, titanium, stainless steel, and ceramic. A heating element 405 such as a stainless steel, titanium, kanthal or nichrome coiled wire is within the furnace. In some instances ceramic heaters or high-temperature co-fired ceramics (HTCC) with metal element layered therein or thereon may be used in place of the coiled wire. Optionally, insulation may wrap at least some of the thin wall of the furnace. A floor 115' is shown substantially closing off the wider base 403 of the furnace. Air intakes 117 are formed through that floor to allow air to pass into the furnace. In some exemplars, between the body 6002 and the furnace 400 is the air insulation zone (AIZ) in which the heat radiating from the exterior wall 429 of the furnace heats the air in the AIZ thereby recycling waste heat (6060) to preheat the intake air which can be recirculated as it is sucked through body vents 6063 to the AIZ then into at least one of an air plenum 6070 or directly into the furnace via the furnace vents 121. The pathway of the preheated air is either the floor vents 120 and into the plenum along arrow 6065 which shows the pathway through floor vents 120 into air plenum 6070. Or directly into the furnace through the furnace vents 121.

During inhalation air is drawn from the exterior of the body through a vent 6063 into the AIZ then moves from the AIZ into at least one of the floor vents 120 and the furnace vents 121. The recycling can reduce power requirements to heat air entering the furnace. In some instance an optional fan 3002 may be placed in the air plenum 6070 in between the chassis and the floor 115'. Aspects of implementations of the accessory module are illustrated in greater detail in FIGS. 9C, 9D and 11-13. Accessory module 6010 is attached at a connection interface 6003 to the body. The connection interface may be via latch/catch, magnet, threaded portions, twist lock or any reversible attachment/fixation means. Those of ordinary skill in the art will recognize that a plethora of attachment means exist and the above is not an exclusive list of those means within the scope of this disclosure.

In some instances the accessory module 6010 has a latch 6080 formed on a portion of the open top region 6020. The latch may be a threaded portion or any other known twist to affix latch and catch combination. In the case of a threaded latch 6080 a cover 6082 for the accessory module mates with the accessory module via a corresponding threaded catch 6084. The cover 6084 has a top wall 6086 to close off the accessory module. A mounting region 6090 is formed at the top of the cover. The mounting region can extend above the top region 6020 and is configured to reversibly mate with the bottom recess portion 6009 to connect the accessory module to the hollow body 6002. A gasket or O-ring 6016 may be added at the mounting region to form an additional seal/odor barrier to reduce or limit the aroma or smell associated with the material chamber or fluid pathway. Those of ordinary skill in the art will recognize that there are a plethora of latch and catch combinations to reversibly connect the accessory module to the body and that a mere design alteration would be within the scope of this disclosure.

FIG. 10 illustrates aspects of a vapor dispenser 9100. A top closure 9101 formed of an insulator plastic or resin such as phenolic resin, silicon, PEEK, ABS or ULTEM has an exterior top wall 9102 through which the exit port 315' extends, a bottom face 9005 and an annular side wall 9106 and a mounting guide (or gap) 9108 whereby the vapor dispenser, mount to the top portion 103 of the body 6002 thereby positioning the material containment that is a top portion cavity 9110 formed in the top closure during molding and having an extended chamber interface 9112 which is a cylindrical region to which the removable bottom cup 900 with its air permeable bottom 910 fits into the "IFA".

The exit port 315' is fluidly connected to the cavity 9110 forming a fluid pathway 9120 for vapor and heated air 2175 (from material in the bottom cup) to exit the device.

FIGS. 11 and 12 show aspects of accessory module 6010 which either form a recess 6009 for a receptacle mounting of a body 6002 or mount with magnetic connections. FIG. 11 illustrates an extended portion 435E of the chassis 435 with an optional O-ring (6094) surrounding it. The bottom of the chassis 435" fits into a recess 6009 formed at the open top 6014 of the accessory module. Optionally a lid or cover 6030 may be used to at least partially seal off the accessory module. In FIG. 12 there is shown a body 6002 and an accessory module 6010 which connect via at least on magnet 6095 and one region that is attractive to a magnet 6097.

FIGS. 13A and 13B show vaporizer with chamber cartridge convection heating system device and method 600. The removable material unit 602 comprises a chamber 603 which is a containment end for material "M" and one of a fixed and removable fluid pathway 604 connected thereto. A flow through divider 605 such as a screen or coarse filter which allows vapors to pass through may be positioned between the containment chamber 603 and the fluid pathway 604 which terminates at the inhalation end 606. One or more dividers 612 may be added to reduce the opportunity for plant material to become disengaged from the containment chamber. The dividers are permeable to air flow. The body 12 contains a furnace, heating element combination forming a convection heating system. The removable material unit 602 fits into an interface 608 which supports an interface gasket 500 which seals against air leakage when the material unit 602 is inserted into the device.

The method of operation includes a PCB "board" with a controller 65 and other PCB components being located inside the body 12 and in signal communication with the on/off switch 68, illumination means 70, and temperature sensor 90. The illumination means being visible on the outside of the body and the on/off switch is visible and accessible from the exterior of the body. The controller controls the power provided to the heating element 405 from the power supply 60 to cause vaporization of material "M" at select temperature(s). The heating element 405 is within a furnace 400. The floor 115' of the furnace is fluidly connected to at least one air intake 117. Side wall air intakes 3000 fluidly connect the exterior of the body 12 to the air intake.

FIG. 15 illustrates a storage and vaporizer system 640 wherein an accessory module 6010 is mated (removably) to the bottom 13 of the case 12. The accessory module has been described in greater detail above.

While the method and agent have been described in terms of what are presently considered to be the most practical implementations and aspects thereof, it is to be understood that the disclosure need not be limited to the disclosed implementations, aspects or order and/or sequence of combination of aspects. It is intended to cover various modifications and similar arrangements included within the spirit and scope of the claims, the scope of which should be accorded the broadest interpretation so as to encompass all such modifications and similar structures. The present disclosure includes any and all implementations of the following claims.

It should also be understood that a variety of changes may be made without departing from the essence of the disclosure. Such changes are also implicitly included in the description. They still fall within the scope of this disclosure. It should be understood that this disclosure is intended to yield a patent covering numerous aspects both independently and as an overall system and in both method and apparatus modes.

Further, each of the various elements of the disclosure and claims may also be achieved in a variety of manners. This disclosure should be understood to encompass each such variation, be it a variation of an implementation of any apparatus implementation, a method or process implementation, or even merely a variation of any element of these.

Particularly, it should be understood that as the disclosure relates to elements of the implementation, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this disclosure is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

In this regard it should be understood that for practical reasons and so as to avoid adding potentially hundreds of claims, the applicant has presented claims with initial dependencies only.

Support should be understood to exist to the degree required under new matter laws—including but not limited to United States Patent Law 35 USC 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternatives.

Further, the use of the transitional phrase "comprising" is used to maintain the "open-end" claims herein, according to traditional claim interpretation. Thus, unless the context requires otherwise, it should be understood that the term "compromise" or variations such as "comprises" or "comprising", are intended to imply the inclusion of a stated element or step or group of elements or steps but not the exclusion of any other element or step or group of elements or steps. Such terms should be interpreted in their most expansive forms so as to afford the applicant the broadest coverage legally permissible. All callouts associated with figures are hereby incorporated by this reference.

Since certain changes may be made in the above system, method, process and or apparatus without departing from the scope of the disclosure herein involved, it is intended that all matter contained in the above description, as shown in the accompanying drawing, shall be interpreted in an illustrative, and not a limiting sense.

It will be understood that various aspects or details of the disclosures may be changed combined, or removed without departing from the scope of the invention. It is not exhaustive and does not limit the claimed inventions to the precise form disclosed. Furthermore, the foregoing description is for the purpose of illustration only, and not for the purpose of limitation. Modifications and variations are possible in light of the above description or may be acquired from practicing the invention. The claims and their equivalents define the scope of the invention.

What is claimed is:

1. A portable aromatherapy vaporizer system comprising:
a generally hollow body (6002) with an open top (103') a recess (6009) above a bottom edge (6008);
a portable power supply (60) inside the body;
a heating system within the body comprising;
a furnace (400);
an air insulation zone (AIZ) between the furnace and hollow body;
a heating element (405) inside the furnace;
a temperature sensor (90);

a controller (65) in signal communication with at least the sensor, heating element, power supply and on/off control (1 OBA);
a floor (115') sealing off the bottom of the furnace;
one or more vents fluidly connecting the AIZ into the furnace;
a connection interface gasket (GIG) (9000) providing a fluid pathway from the open top to the top (402) of the furnace;
a vapor dispenser (8000) including an insulator body (8001) and material chamber (310) having a shaped portion (311) and a bottom cup portion (900), the bottom portion configured to removably mate with the GIG through the open top and the vapor dispenser configured to reversibly attach to the open top;
whereby the on/off switch is in signal communication with the control board and the control board controls the heating of the heating element based on input from the temperature sensor via the heating element; and,
wherein during operation heated air within the heating system moves from the heating element to an air buffer region (4000) and collects until a pressure differential causes the heated air (2150) to move into the material chamber through material (M) thereby producing vapor and heated air (2175).

2. The aromatherapy vaporizer of claim 1 wherein the vapor dispenser is one of refillable and disposable.

3. The vaporizer of claim 1 further comprising a generally hollow accessory module (6010) configured to mate with the recess (6009) and having an open top region (6020), closed bottom (6011) and of a size and shape to contain at least the vapor dispenser and tube (7010).

4. The vaporizer of claim 1 further comprising at least one illumination communication means (70/110) in signal communication with the control board which produces an illumination visible on the exterior of the body.

5. The vaporizer of claim 1 further comprising a fan (3002) to direct air into the vented (117) floor (115') to the interior of the furnace.

6. The vaporizer of claim 5 further comprising a second on/off control (1088) whereby both the heating element and the fan are switched on when that control is activated.

7. The vaporizer of claim 1 the material chamber (310) further comprising:
a shaped container (311) fluidly connected to an exit port (315);
a bottom cup (900); and,
wherein the material chamber is removably fixed within the insulator body; and,
wherein the bottom cup is held above the bottom face (8004) of the insulator body.

8. The vaporizer of claim 1 further comprising at least one airflow sensor (92) in signal communication with the controller.

9. A portable aromatherapy vaporizer comprising:
a generally hollow cylindrical body with an open bottom, a bottom edge (204) and an open top;
a furnace (400) with a bottom region (408) and an upper furnace (409), having a floor closing one end and a heating element inside the furnace;
an air insulation zone (AIZ) between the furnace and hollow body;
a generally tubular chamber interface gasket (CIG) (500) with two open ends providing a fluid pathway from the open upper furnace;
a chamber (310) configured to removably mate with the open end of the CIG;
a removable fluid pathway (300) connected to the chamber;
one or more vents fluidly connecting the AIZ into the furnace;
a chassis (435) having a top (435') and a bottom (435") affixed within the body;
a PCB (board) with a controller (65) and battery supply affixed to the chassis;
a temperature sensor (90) in thermal communication with the furnace and in signal communication with the controller (65);
an on/off switch on the body's exterior in signal communication with the controller;
a recess formed near the bottom edge defined by the chassis bottom affixed above the bottom edge; and,
wherein the recess forms a receptacle which is used to mate an accessory module.

10. The portable aromatherapy vaporizer of claim 9 further comprising an accessory module which reversibly mates with the body at the recess.

11. The vaporizer of claim 10 further comprising a lid (6030) to seal off the top of the accessory module.

12. The portable aromatherapy vaporizer of claim 9 the chassis further comprising a bottom face (437) which contains at least one of an interface display (125), a power data/power interface (132) and inputs (128), power jack (134) each in signal communications with the PCB and controller.

13. The portable aromatherapy vaporizer of claim 9 wherein the open top is a first diameter and the open bottom is a second diameter, the first diameter being smaller than the second diameter.

14. The portable aromatherapy vaporizer of claim 9 wherein the controller is in signal communication with the on/off switch, temperature sensor and heating element; and,
wherein the controller controls the flow of electricity to the heating element from the power supply based on input from the temperature sensor.

15. The portable aromatherapy vaporizer of claim 9 wherein during operation heated air (2150) within the furnace fills an air buffer region (4000) and collects until a pressure differential from inhalation or a fan causes the heated air to move into the material chamber through material (M) thereby producing vapor and heated air (2175).

16. The portable aromatherapy vaporizer of claim 9 further comprising an illumination means in signal communication with the controller which selectively produces an illumination visible on the exterior of the body.

17. A method of ameliorating smell associated with vaporizing organic material, the method comprising:
a sealable generally odor impervious accessory module reversibly mounted to a body;
a body containing heated air (2150) producing system fluidly connected to a vapor dispenser;
a controller in signal communication with the heat producing system to control the temperature of the heat air;
a means to mount the accessory module to the body;
wherein the accessory module is large enough to contain the vapor dispenser; and,
whereby any smell associated with vaporized materials on the vapor dispenser are reduced by virtue of sealing the vapor dispenser in the accessory module.

* * * * *